(12) United States Patent
Sholev et al.

(10) Patent No.: US 9,510,846 B2
(45) Date of Patent: Dec. 6, 2016

(54) ARTICULATING MEDICAL INSTRUMENT

(75) Inventors: Mordehai Sholev, Moshav Amikam (IL); Nir Lilach, Moshav Kfar Yehoshua (IL); Ram Grossfeled, Haifa (IL); Eliahu Eliachar, Haifa (IL); Gilad Lavi, Rishon-LeZion (IL); Gilad Heftman, Kibbutz Ein-Gev (IL)

(73) Assignee: Artack Medical (2013) Ltd., Maccabim-Reut (IL)

( * ) Notice: Subject to any disclaimer, the term of this patent is extended or adjusted under 35 U.S.C. 154(b) by 0 days.

(21) Appl. No.: 13/543,960

(22) Filed: Jul. 9, 2012

(65) Prior Publication Data

US 2012/0271285 A1 Oct. 25, 2012

Related U.S. Application Data

(63) Continuation of application No. PCT/IL2011/000089, filed on Jan. 26, 2011.

(Continued)

(51) Int. Cl.
*A61B 17/29* (2006.01)
*A61B 17/068* (2006.01)
(Continued)

(52) U.S. Cl.
CPC ............ *A61B 17/29* (2013.01); *A61B 17/068* (2013.01); *A61B 10/0045* (2013.01);
(Continued)

(58) Field of Classification Search
CPC .................. A61B 18/1445; A61B 2017/2929; A61B 2017/2927
(Continued)

(56) References Cited

U.S. PATENT DOCUMENTS

| 4,950,273 A | 8/1990 | Briggs |
| 5,209,747 A | 5/1993 | Knoepfler |

(Continued)

FOREIGN PATENT DOCUMENTS

| DE | 8535164 | 2/1986 |
| EP | 1842500 | 10/2007 |

(Continued)

OTHER PUBLICATIONS

Communication Relating to the Results of the Partial International Search Dated Jun. 6, 2011 From the International Searching Authority Re. Applicaiton No. PCT/IL/2011/000089.

(Continued)

*Primary Examiner* — Aaron Roane

(57) ABSTRACT

An articulating medical instrument comprising of:
  a substantially straight proximal segment;
  a substantially straight distal segment;
  an articulation mechanism having a straight configuration in which the proximal and distal segments form a substantially straight line and at least one articulated configuration in which the proximal and distal segments form an articulation angle of less than 180 degrees between the segments, the articulation mechanism being configured for increasing or decreasing the articulation angle; and
  one or more drive mechanisms configured for transferring force from the proximal segment to the distal segment, wherein the drive mechanism does not follow substantially straight lines between the proximal and distal segments passing through the apex of the articulation angle.

29 Claims, 32 Drawing Sheets

Related U.S. Application Data

(60) Provisional application No. 61/298,238, filed on Jan. 26, 2010, provisional application No. 61/389,303, filed on Oct. 4, 2010.

(51) Int. Cl.
| | | |
|---|---|---|
| A61B 10/00 | (2006.01) | |
| A61B 17/00 | (2006.01) | |
| A61B 17/064 | (2006.01) | |
| A61M 5/315 | (2006.01) | |

(52) U.S. Cl.
CPC .............. *A61B 2017/00398* (2013.01); *A61B 2017/00898* (2013.01); *A61B 2017/0648* (2013.01); *A61B 2017/2902* (2013.01); *A61B 2017/2903* (2013.01); *A61B 2017/2927* (2013.01); *A61B 2217/005* (2013.01); *A61M 5/31581* (2013.01)

(58) Field of Classification Search
USPC ...................................... 606/1; 600/141–143
See application file for complete search history.

(56) References Cited

U.S. PATENT DOCUMENTS

| | | | |
|---|---|---|---|
| 5,254,130 A | 10/1993 | Poncet et al. | |
| 5,271,543 A | 12/1993 | Grant et al. | |
| 5,312,023 A | 5/1994 | Green et al. | |
| 5,330,502 A | 7/1994 | Hassler et al. | |
| 5,370,650 A | 12/1994 | Tovey et al. | |
| 5,381,943 A | 1/1995 | Allen et al. | |
| 5,465,894 A | 11/1995 | Clark et al. | |
| 5,501,654 A | 3/1996 | Failla et al. | |
| 5,549,637 A | 8/1996 | Crainich | |
| 5,575,799 A | 11/1996 | Bolanos et al. | |
| 5,578,048 A | 11/1996 | Pasqualucci et al. | |
| 5,643,294 A | 7/1997 | Tovey et al. | |
| 5,680,982 A | 10/1997 | Schulze et al. | |
| 5,704,534 A | 1/1998 | Huitema et al. | |
| 5,823,066 A | 10/1998 | Huitema et al. | |
| 5,901,895 A | 5/1999 | Heaton et al. | |
| 5,907,664 A | 5/1999 | Wang et al. | |
| 6,132,441 A | 10/2000 | Grace | |
| 6,171,316 B1 | 1/2001 | Kovac et al. | |
| 6,250,532 B1 | 6/2001 | Green et al. | |
| 6,464,711 B1 | 10/2002 | Emans et al. | |
| 6,663,641 B1 | 12/2003 | Kovac et al. | |
| 6,666,854 B1 | 12/2003 | Lange et al. | |
| 6,743,239 B1 | 6/2004 | Kuehn et al. | |
| 6,817,974 B2 | 11/2004 | Cooper et al. | |
| 6,931,613 B2 | 8/2005 | Kauth et al. | |
| 6,964,363 B2 | 11/2005 | Wales et al. | |
| 6,964,668 B2 | 11/2005 | Modesitt et al. | |
| 6,969,385 B2 | 11/2005 | Moreyra | |
| 6,981,628 B2 | 1/2006 | Wales | |
| 6,991,627 B2 | 1/2006 | Madhani et al. | |
| 7,087,071 B2 * | 8/2006 | Nicholas et al. | 606/206 |
| 7,090,637 B2 | 8/2006 | Danitz et al. | |
| 7,135,030 B2 | 11/2006 | Schwemberger et al. | |
| 7,235,087 B2 | 6/2007 | Modesitt et al. | |
| 7,291,161 B2 | 11/2007 | Hooven | |
| 7,316,681 B2 | 1/2008 | Madhani et al. | |
| 7,347,863 B2 | 3/2008 | Rothe et al. | |
| 7,391,173 B2 | 6/2008 | Schena | |
| 7,398,707 B2 | 7/2008 | Morley et al. | |
| 7,410,483 B2 | 8/2008 | Danitz et al. | |
| 7,422,592 B2 | 9/2008 | Morley et al. | |
| 7,481,348 B2 | 1/2009 | Marczyk | |
| 7,500,979 B2 | 3/2009 | Hueil et al. | |
| 7,506,790 B2 | 3/2009 | Shelton, IV | |
| 7,543,730 B1 | 6/2009 | Marczyk | |
| 7,543,731 B2 | 6/2009 | Green et al. | |
| 7,549,563 B2 | 6/2009 | Mather et al. | |
| 7,549,998 B2 | 6/2009 | Braun | |
| 7,553,275 B2 | 6/2009 | Padget et al. | |
| 7,584,880 B2 | 9/2009 | Racenet et al. | |
| 7,588,177 B2 | 9/2009 | Racenet | |
| 7,608,083 B2 | 10/2009 | Lee et al. | |
| 7,615,066 B2 | 11/2009 | Danitz et al. | |
| 7,648,055 B2 | 1/2010 | Marczyk | |
| 7,654,431 B2 | 2/2010 | Hueil et al. | |
| 7,670,284 B2 | 3/2010 | Padget et al. | |
| 7,670,334 B2 | 3/2010 | Hueil et al. | |
| 7,673,780 B2 | 3/2010 | Shelton, IV et al. | |
| 2004/0049227 A1 | 3/2004 | Jervis | |
| 2005/0033357 A1 | 2/2005 | Braun | |
| 2005/0033358 A1 | 2/2005 | Suzuki | |
| 2005/0043582 A1 | 2/2005 | Stokes | |
| 2005/0251165 A1 | 11/2005 | Vaughan et al. | |
| 2005/0273084 A1 | 12/2005 | Hinman et al. | |
| 2006/0069396 A1 * | 3/2006 | Meade et al. | 606/144 |
| 2006/0094931 A1 | 5/2006 | Danitz et al. | |
| 2006/0111210 A1 | 5/2006 | Hinman | |
| 2007/0038220 A1 | 2/2007 | Shipp | |
| 2007/0039996 A1 | 2/2007 | Mather et al. | |
| 2007/0167702 A1 | 7/2007 | Hasser et al. | |
| 2007/0221700 A1 | 9/2007 | Ortiz et al. | |
| 2007/0250064 A1 | 10/2007 | Darois et al. | |
| 2007/0250111 A1 | 10/2007 | Lu et al. | |
| 2007/0287992 A1 | 12/2007 | Diolaiti et al. | |
| 2008/0029574 A1 | 2/2008 | Shelton et al. | |
| 2008/0065102 A1 | 3/2008 | Cooper | |
| 2008/0086154 A1 | 4/2008 | Taylor et al. | |
| 2008/0086854 A1 | 4/2008 | Boyd et al. | |
| 2008/0103524 A1 | 5/2008 | Grace | |
| 2008/0147113 A1 | 6/2008 | Nobis et al. | |
| 2008/0262492 A1 | 10/2008 | Lee | |
| 2008/0296343 A1 | 12/2008 | Schall et al. | |
| 2008/0312668 A1 | 12/2008 | Grace | |
| 2009/0065549 A1 | 3/2009 | Viola | |
| 2009/0114699 A1 | 5/2009 | Viola | |
| 2009/0114700 A1 | 5/2009 | Marczyk | |
| 2009/0156995 A1 | 6/2009 | Martin et al. | |
| 2009/0182354 A1 | 7/2009 | Blier et al. | |
| 2009/0188965 A1 | 7/2009 | Levin et al. | |
| 2009/0206128 A1 | 8/2009 | Hueil et al. | |
| 2009/0206137 A1 | 8/2009 | Hall et al. | |
| 2009/0222022 A1 | 9/2009 | Laporte Rosello et al. | |
| 2009/0248053 A1 | 10/2009 | Bacher et al. | |
| 2009/0277947 A1 | 11/2009 | Viola | |
| 2009/0283568 A1 | 11/2009 | Racenet et al. | |
| 2009/0308908 A1 | 12/2009 | Green et al. | |
| 2010/0001038 A1 | 1/2010 | Levin et al. | |
| 2010/0038403 A1 | 2/2010 | D'Arcangelo | |
| 2010/0051669 A1 | 3/2010 | Milliman | |

FOREIGN PATENT DOCUMENTS

| | | |
|---|---|---|
| EP | 2036505 | 3/2009 |
| FR | 2682877 | 4/1993 |
| JP | 2007-275565 | 10/2007 |
| JP | 2009-505688 | 2/2009 |
| JP | 2009-506804 | 2/2009 |
| JP | 2009-066400 | 4/2009 |
| JP | 2009-534100 | 9/2009 |
| WO | WO 01/00095 | 1/2001 |
| WO | WO 03/099134 | 12/2003 |
| WO | WO 2006/057702 | 6/2006 |
| WO | WO 2006/073581 | 7/2006 |
| WO | WO 2006/093975 | 9/2006 |
| WO | WO 2007/018898 | 2/2007 |
| WO | WO 2007/104397 | 9/2007 |
| WO | WO 2007/114975 | 10/2007 |
| WO | WO 2007/123978 | 11/2007 |
| WO | WO 2007/146842 | 12/2007 |
| WO | WO 2008/131046 | 10/2008 |
| WO | WO 2009/055105 | 4/2009 |
| WO | WO 2009/088690 | 7/2009 |
| WO | WO 2009/100366 | 8/2009 |
| WO | WO 2009/126955 | 10/2009 |

(56) References Cited

FOREIGN PATENT DOCUMENTS

WO     WO 2009/155220     12/2009
WO     WO 2010/009525     1/2010

OTHER PUBLICATIONS

International Preliminary Report on Patentability Dated May 22, 2012 From the International Preliminary Examining Authority Re. Application No. PCT/IL2011/000089.
International Search Report and the Written Opinion Dated Jul. 15, 2011 From the International Searching Authority Re. Application No. PCT/IL/2011/000089.
Response Dated Sep. 20, 2011 to International Search Report and the Written Opinion of Jul. 15, 2011 From the International Searching Authority Re. Applicaiton No. PCT/IL2011/000089.
Second Written Opinion Dated Jan. 16, 2012 From the International Preliminary Examining Authority Re. Application No. PCT/IL2011/000089.
Office Action Dated Dec. 4, 2014 From the Israel Patent Office Re. Application No. 221109.
Translation Dated Jan. 26, 2015 of Office Action Dated Dec. 4, 2014 From the Israel Patent Office Re. Application No. 221109.
Notice of Reason for Rejection Dated Sep. 12, 2014 From the Japanese Patent Office Re. Application No. 2012-550566 and Its Translation Into English.

* cited by examiner

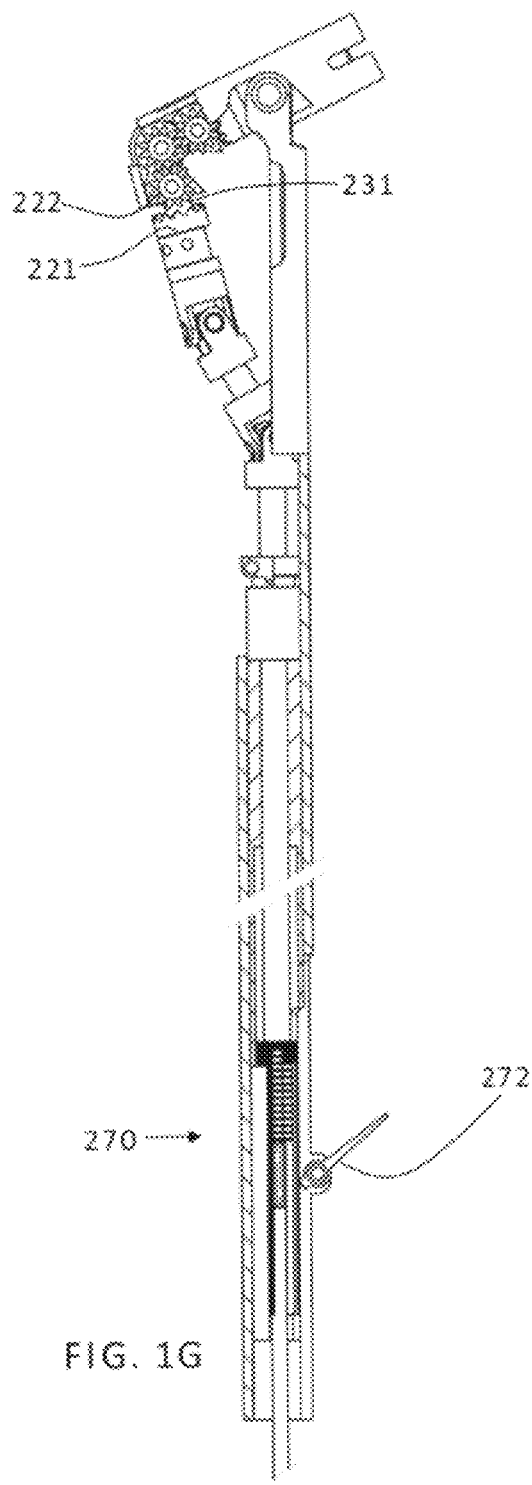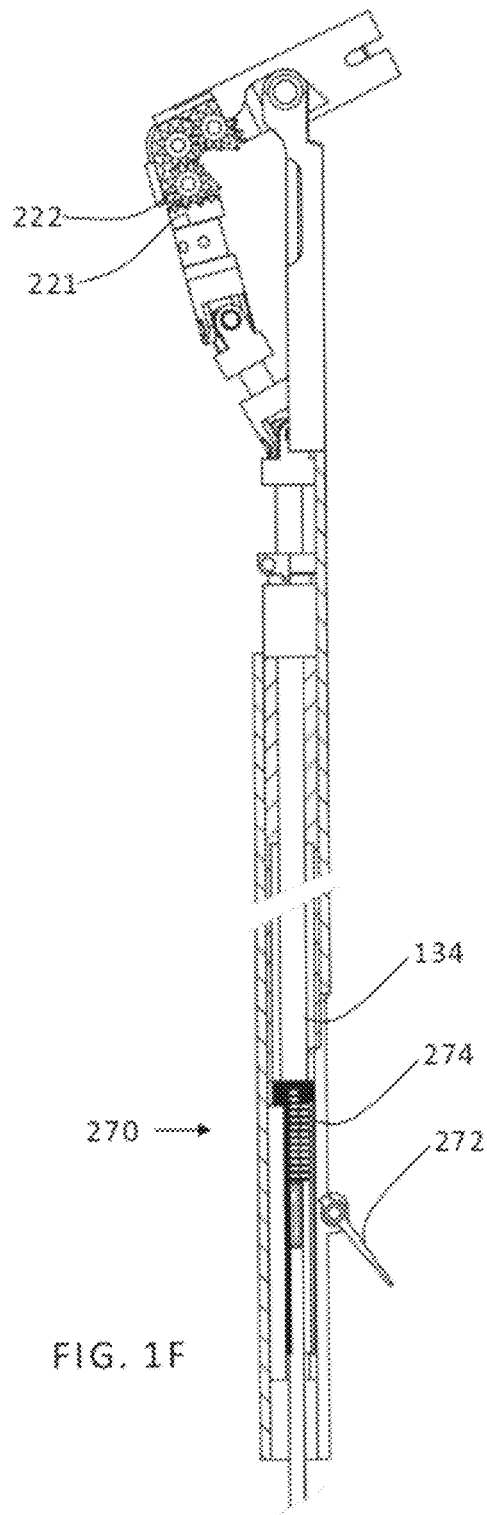

ARTICULATING MEDICAL INSTRUMENT

RELATED APPLICATIONS

This application is a continuation of PCT Patent Application No. PCT/IL2011/000089 having International filing date of Jan. 26, 2011, which claims the benefit of priority of U.S. Provisional Patent Application Nos. 61/298,238 filed on Jan. 26, 2010 and 61/389,303 filed on Oct. 4, 2010. The contents of the above applications are all incorporated herein by reference in their entirety.

FIELD AND BACKGROUND OF THE INVENTION

The present invention, in some embodiments thereof, relates to an articulating medical instrument and, more particularly, but not exclusively, to an articulating medical instrument having a drive mechanism.

A number of articulating medical instruments and methods are known in the art.

U.S. Pat. No. 6,913,613 to Schwarz et al. describes a surgical instrument having a hollow shank having a proximal end and a distal end, an actuating device arranged in the proximal end, and an instrument tip bendable or pivotal toward the shank which carries a mouth part arranged at the distal end thereof. A gear mechanism is further provided which transforms at least a first movement of the actuating device into a rotation of the mouth part according to a first specific transmission ratio in relation to the first actuating movement. The gear mechanism mechanically couples the actuating device to the instrument tip.

U.S. Pat. No. 7,087,071 to Nicholas et al describes a surgical instrument for use in endoscopic or laparoscopic procedures. The instrument includes a handle portion, an endoscopic portion extending from the handle portion, an articulating section pivotably connected to a distal end portion of the endoscopic portion, and a retractor assembly operatively associated with the articulating section. Structure is provided for manipulating the articulating section relative to the longitudinal axis of the endoscopic portion within an angular degree of rotation. A link rod is connecting between the articulating section and the endoscopic portion, wherein during manipulation of the articulating section, the link rod may be positioned out of the axis between the articulating section and the endoscopic portion.

U.S. Pat. No. 5,549,637 to Crainich describes an articulated medical instrument which comprises a handle, an elongate body member terminating in a tool head receiver and up to three joints, each pivotable to about 60°, whereby the tool head receiver is pivotable up to a total of 180° relative to the straight position thereof.

U.S. 2010/0001038 to Levin et al describes a pivoting tacker for applying surgical fasteners such as rotary tacks, where the tacks pass through a pivoting structure, including a plurality of pivoting links, each including a link shaft.

U.S. Pat. No. 3,995,449 describes a joint for homokynetic transmission of rotary motion between two concurrent shafts on which head portions are mounted. The head portions are connected by pairs of articulated driving-rods, each slidably and rotatedly disposed in a respective bore in a respective head portion. All the pairs of rods ensure the rotary transmission, and both head portions are also hinge-coupled with double articulation line by means of coupling-boxes loosely mounted on the head portions.

Additional background art includes U.S. Pat. No. 7,673,780, U.S. 2009/0065549, U.S. 2008/0296343, U.S. Pat. No. 5,578,048, U.S. Pat. No. 7,549,998, U.S. Pat. No. 5,209,747, U.S. Pat. No. 1,334,388 and EP 0 042 330.

SUMMARY OF THE INVENTION

An aspect of some embodiments of the invention relates to an articulating medical instrument, having a proximal segment and a distal segment, the distal segment being configured for holding a medical tool at an end portion thereof and/or for containing surgical objects. A drive mechanism is provided for actuating the medical tool and/or objects. In some embodiments, the drive mechanism does not follow substantially straight lines between the proximal and distal segments passing through the apex of the articulation angle between the distal segment and the proximal segment of the instrument when articulated. In some embodiments, the instrument further comprises an articulation mechanism for articulating the distal segment towards the proximal segment.

According to an aspect of some embodiments of the present invention there is provided an articulating medical instrument comprising of:

a substantially straight proximal segment;

a substantially straight distal segment;

an articulation mechanism having a straight configuration in which the proximal and distal segments form a substantially straight line and at least one articulated configuration in which the proximal and distal segments form an articulation angle of less than 180 degrees between the segments, the articulation mechanism being configured for increasing or decreasing the articulation angle; and one or more drive mechanisms configured for transferring force from the proximal segment to the distal segment, wherein the drive mechanism does not follow substantially straight lines between the proximal and distal segments passing through the apex of the articulation angle.

According to some embodiments of the invention, at least one drive mechanism does not pass through the apex of the articulation angle.

According to some embodiments of the invention, at least one drive mechanism is positioned interior of the articulation angle.

According to some embodiments of the invention, the articulation mechanism comprises a lever and wherein the at least one drive mechanism is positioned between the articulation angle and the lever.

According to some embodiments of the invention, at least one drive mechanism is positioned exterior of the articulation angle.

According to some embodiments of the invention, the articulation mechanism comprises a lever extending out of the proximal segment and wherein the drive mechanism is positioned between the lever and the proximal segment.

According to some embodiments of the invention, at least one drive mechanism is configured to transfer rotary movement from a proximal end of the instrument to a distal end of the instrument.

According to some embodiments of the invention, at least one drive mechanism is configured to transfer linear movement from a proximal end of the instrument to a distal end of the instrument.

According to some embodiments of the invention, a medical tool is positioned in or at the distal segment and wherein the drive mechanism is configured to actuate the medical tool.

According to some embodiments of the invention, the instrument further comprises a sheath covering the articulation mechanism and the drive mechanism.

According to some embodiments of the invention, the drive mechanism comprises a gear mechanism.

According to some embodiments of the invention, the drive mechanism comprises a flexible shaft.

According to some embodiments of the invention, the proximal and distal segments are connected by a flexible joint.

According to some embodiments of the invention, the drive mechanism and articulation mechanism are not fixedly connected at the connection between the proximal and distal segments.

According to some embodiments of the invention, the drive mechanism is not substantially affected by external forces responsive applied against maintaining the articulation angle.

According to some embodiments of the invention, the instrument further comprises a distance compensation mechanism for compensating the distance at the point of attachment of the drive mechanism to the distal and proximal segments in the articulated configuration as the articulation angle changes.

According to some embodiments of the invention, the instrument further comprises a handle attached to the proximal segment, wherein the drive and articulation mechanism are controllable from the handle.

According to some embodiments of the invention, the instrument further comprises an adaptor for attaching the instrument to an existing handle.

According to an aspect of some embodiments of the present invention there is provided an articulating medical instrument comprising of:

a substantially straight proximal segment;

a substantially straight distal segment, the distal segment containing a threaded shaft around which a plurality of helical fasteners are screwed;

an articulation mechanism having a straight configuration in which the proximal and distal segments form a substantially straight line and at least one articulated configuration in which the proximal and distal segments form an articulation angle of less than 180 degrees between the segments or extensions of the segments, the articulation mechanism being configured for articulating the distal segment towards or away from the proximal segment; and a drive mechanism configured for transferring rotary movement from the proximal segment to the distal segment such that the fasteners distally exit the threaded shaft, wherein the drive mechanism does not follow substantially straight lines between the proximal and distal segments passing through the apex of the articulation angle.

According to an aspect of some embodiments of the present invention there is provided an articulating medical instrument comprising of:

a substantially straight proximal segment;

a substantially straight distal segment, the distal segment containing:

a plurality of threaded fasteners comprising wings;

a tube having longitudinal slots in which the helical fasteners are positioned such that the wings exit through the slots; and an internally threaded outer layer into which the wings of the fasteners are screwed;

an articulation mechanism having a straight configuration in which the proximal and distal segments form a substantially straight line and at least one articulated configuration in which the proximal and distal segments form an articulation angle of less than 180 degrees between the segments or extensions of the segments, the articulation mechanism being configured for articulating the distal segment towards or away from the proximal segment; and a drive mechanism configured for transferring rotary movement from the proximal segment to the distal segment such that the tube rotates causing the fasteners to exit the distal segment, wherein the drive mechanism does not follow substantially straight lines between the proximal and distal segments passing through the apex of the articulation angle.

According to some embodiments of the invention, the drive mechanism is positioned exterior of the articulation angle.

According to some embodiments of the invention, the articulation mechanism comprises a lever and wherein the drive mechanism is positioned between the articulation angle and the lever.

According to some embodiments of the invention, the drive mechanism is positioned interior of the articulation angle.

According to some embodiments of the invention, the articulation mechanism comprises a lever extending out of the proximal segment and wherein the drive mechanism is positioned between the articulation angle and the proximal segment.

According to an aspect of some embodiments of the present invention there is provided an articulating rotary coupler comprising:

a proximal shaft and a distal shaft;

a plurality of rod pairs comprising a plurality of proximal rods connected to the proximal shaft and a plurality of distal rods connected to the distal shaft, where the proximal rods and distal rods are interconnected by a planar joint, such that the rotary coupler comprises a straight configuration in which the distal shaft and proximal shaft form a substantially straight line and an articulated configuration in which the distal shaft is articulate around the planar joint towards the proximal shaft; and an alignment mechanism for aligning the rod pairs such that the distal shaft can articulate around the planar joint at any rotational position of the shafts in the straight configuration.

According to some embodiments of the invention, the alignment mechanism comprises:

a plurality of cylindrical housings in which extensions of the rods are slidably inserted, the housings including an axle positioned eccentric of an axis of the housings;

a disk in which the knobs are positioned, the disk being positioned eccentric of the proximal shaft.

According to some embodiments of the invention, the alignment mechanism comprises springs between the rods and the inside of the ends of the housings.

According to some embodiments of the invention, the alignment mechanism is attached to the proximal shaft.

According to some embodiments of the invention, a plurality of rod pairs comprises at least three rod pairs.

According to an aspect of some embodiments of the present invention there is provided an articulating rotary coupler comprising:

a proximal shaft and a distal shaft;

a plurality of rod pairs comprising a plurality of proximal rods connected to the proximal shaft and a plurality of distal rods connected to the distal shaft, where the proximal rods and distal rods are interconnected by a flexible element, such that the rotary coupler comprises a straight configuration in which the distal shaft and proximal shaft form a substantially straight line and an articulated configuration in which the distal shaft is articulate around the flexible element towards the proximal shaft.

According to some embodiments of the invention, the rotary coupler further comprises a linear compensation mechanism for the plurality of rod pairs.

According to some embodiments of the invention, the linear compensation mechanism comprises springs attached to an end of the rod pairs.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1H are schematic illustrations of an articulating surgical instrument according to an exemplary embodiment of the invention;

DESCRIPTION OF SPECIFIC EMBODIMENTS OF THE INVENTION

Figure 1A:
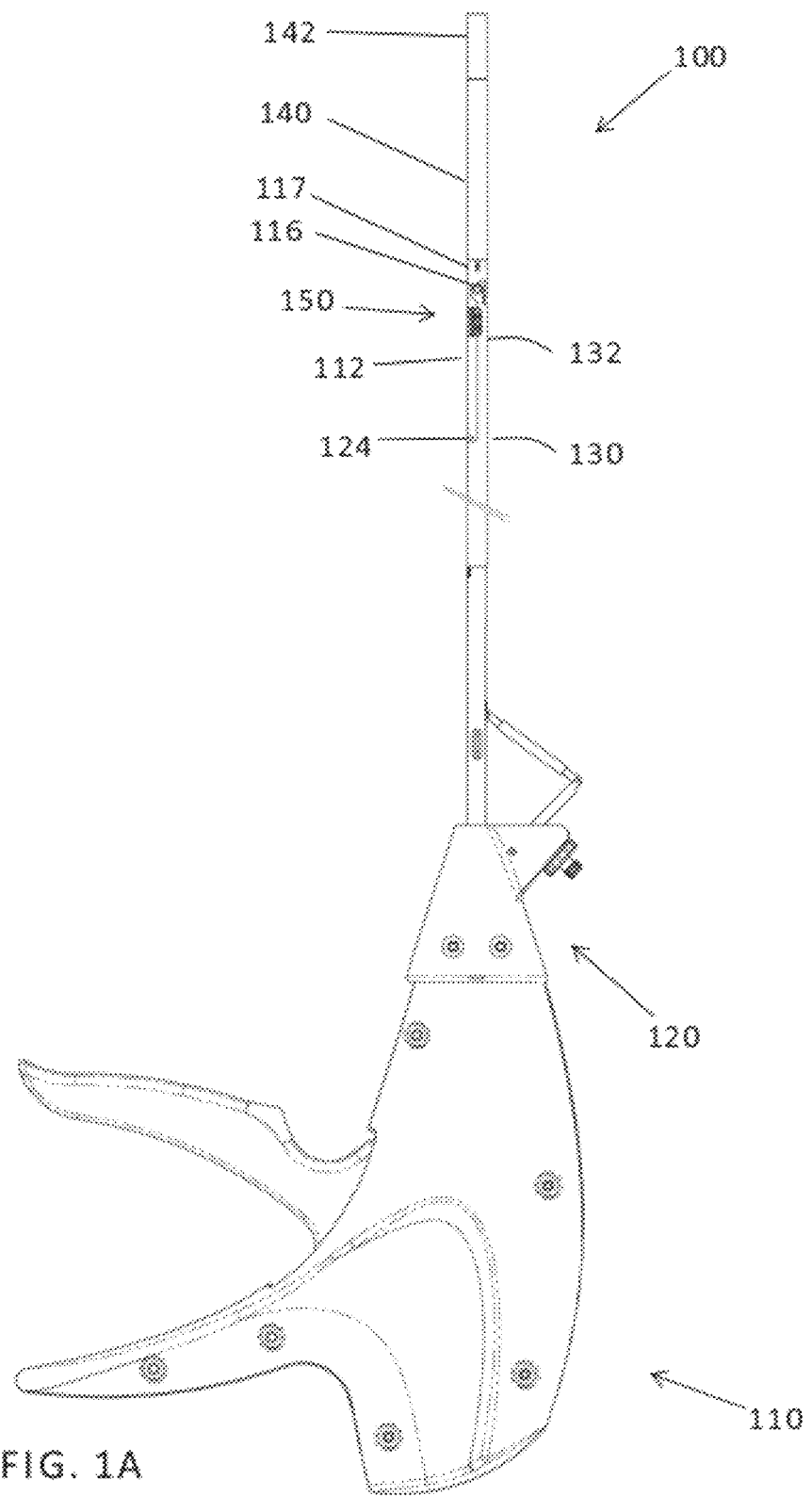

The present invention, in some embodiments thereof, relates to an articulating medical instrument and, more particularly, but not exclusively, to an articulating medical instrument having a drive mechanism.

Some embodiments of the invention relate to a medical instrument having a proximal segment and a distal segment. The instrument has a straight configuration in which the proximal segment and distal segment form a substantially straight line in which the proximal and distal segment form an angle of substantially 180 degrees form between the segments, and an articulated configuration, in which the proximal and distal portions form an articulation angle of less than 180° between the segments or extensions of the segments.

The instrument is configured for containing or carrying medical tools and/or surgical objects at the distal segment. Optionally, medical tools and/or surgical objects (hereinafter, referred to collectively as "medical tools") are contained within the distal segment. Alternatively or additionally, one or more medical tool are attached to an end of the distal segment. Alternatively or additionally, the medical tool(s) can be inserted into the distal portion during maneuvering thereof and deployed when needed. Alternatively or additionally, a conduit or the like is inserted through the proximal and distal segments for injection of medication or collecting of tissue samples.

An aspect of some embodiments of the invention relates to a drive mechanism for actuating the medical tool. Preferably the drive mechanism is controllable from the proximal segment of the instrument, or from a handle or adaptor attached to the proximal segment. In some embodiments of the invention, the drive mechanism does not follow substantially straight lines between the proximal and distal segments passing through the apex of the articulation angle in the articulated configuration. In some embodiments, the drive mechanism does not pass through the apex of the articulation angle formed by the proximal segment and the distal segment in the articulated configuration.

As used herein, the term "drive mechanism" comprises a mechanism that transfers torque or force from the proximal segment to the distal segment, thereby actuating a medical tool or tools at or in the distal segment. For example, rotating a medical tool or surgical instrument, controlling medical forceps or scissors, actuating a tacker, injecting medication, collecting tissue samples, etc. In some embodiments, the drive mechanism transfers rotary motion. Alternatively or additionally, the drive mechanism transfers linear movement, for example, pulling or pushing a medical instrument or actuating an instrument by pulling or pushing. Exemplary drive mechanisms are springs, rods, cardan joints, gears, cables or flexible shafts. In some embodiments, the drive mechanism consists of two actuation mechanisms which may be positioned one inside the other, for example a flexible shaft configured for transfer of rotary movement with a wire passing through the shaft, the wire configured for transfer of linear movement. Optionally, more than one wire or actuation device is positioned in an additional actuation mechanism As used herein, the articulation angle is an angle of less than 180 degrees formed by the substantially straight distal segment and substantially straight proximal segment in the articulated configuration. In some embodiments, the proximal segment comprises parts deviating from the substantially straight segment (such as a lever), these extending parts are not considered when defining the articulation angle. Optionally, a hinge forming the angle is provided in the instrument. Alternatively, such a hinge is not physically present in the instrument and the axes of the straight segments are continued to define the articulation angle.

As used herein, the "articulated configuration" refers to any configuration in which proximal segment and distal segment do not form a substantially straight line. Optionally, the articulated configuration refers to a configuration in which the articulation angle is more than 0° and less than 180°, i.e. any angle between 1°-179°, for example, 120°, 60°, 45°, 8° or intermediate values. The articulation configuration refers to articulation of the proximal and distal segments on a single plane. It is understood that the instrument, including both segments, can rotate around its axis at any articulated configuration.

There is further provided an articulation mechanism, configured for articulating the distal segment towards or away from the proximal segment. In some embodiments, the articulation mechanism is a lever mechanism. In some embodiments, the lever mechanism includes a sliding lever located in or attached to the proximal segment. The lever may be pushed in order to articulate the distal segment towards the proximal segment and be pulled in order to articulate the distal segment away from the proximal segment.

In some embodiments, the lever mechanism includes a sliding lever attached at one end to the distal segment and on its other end to the proximal segment. The lever may be pulled in order to articulate the distal segment towards the proximal segment and be pushed in order to articulate the distal segment away from the proximal segment.

Optionally, the lever is positioned interior of the articulation angle. Alternatively, the lever is positioned exterior of the articulation angle.

In some embodiments, a hinge or joint connecting the ends of the proximal and distal segments is provided around which the distal segment articulates. Alternatively, the ends of the distal and proximal segments are connected by a flexible hinge, such as a flexible shaft, spring, etc.

Optionally, the drive mechanism starts at the proximal segment (generally at or near its distal end) and ends in the distal segment (generally at or near its proximal end). In passing between these segments it may be positioned between the lever and the articulation angle in the articulated configuration. In some embodiments of the invention, in the articulated configuration the drive mechanism is bent throughout at a less sharp angle than the articulation angle. In some embodiments, the drive mechanism is situated interior of the articulation angle, for example when the lever is situated interior of the articulation angle. In other embodiments, the drive mechanism is situated exterior of the articulation angle, for example, when the lever is situated exterior of the articulation angle. In some embodiments, the drive mechanism is positioned on a different plane than the articulation angle.

The drive mechanism and/or articulation mechanism may be positioned in or parallel to the substantially straight instrument when in its straight configuration and extend from the segments in an articulated configuration.

In some embodiments of the invention, at the articulation angle, parts of the drive mechanism are not fixedly connected to parts of the articulation mechanism, whereby forces involved in changing the articulation angle or in maintaining the articulation angle have no or minimal effect on the drive mechanism.

In some embodiments of the invention, a distance compensation mechanism is provided for compensating the distance at the point of attachment of the drive mechanism to the distal and proximal segments in the articulated configuration as the articulation angle changes.

In some embodiments of the invention, the instrument further comprises a sheath covering the drive mechanism and lever in order to prevent body tissues from being caught in the mechanisms. In some embodiments the sheath optionally also covers the hinge.

An aspect of some embodiments of the invention relates to an articulating coupler for coupling a first and second shafts (or segments), where the shafts freely rotate and can articulate towards each other at any rotational position. The rotary coupler comprises a plurality of rod pairs including a plurality of first rods connected to the first shaft and a plurality of second rods connected to the second shaft. The first and second rods in a pair are preferably interconnected by a planar hinge or joint for articulating the shafts. An alignment mechanism is provided for aligning the planar hinge of the plurality of rod pairs such that the rod pairs can articulate in a same direction, for any rotational position of the rotary coupler.

In some embodiments, the alignment mechanism consists of a plurality of circular housings having longitudinal slots in which extensions of the first (or second) rods fit, thereby preventing undesired rotation of the rod pairs around their axes. The housings each include an axle which is eccentric to the circular housing, which is connected to a circular disk, positioned eccentric to the first shaft. The eccentric position of the axles is substantially equal to and are in the same direction as the eccentric position of the disk. Due to the eccentric position of the knobs and disk, as the disk rotates, the direction of the slots remains the same and is the same for all the slots.

An aspect of some embodiments of the invention, relates to an articulating rotary coupler, where the rod pairs are interconnected by a flexible element.

These rotary couplers described above may be used as a combination drive and articulation mechanism in the embodiments described above.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
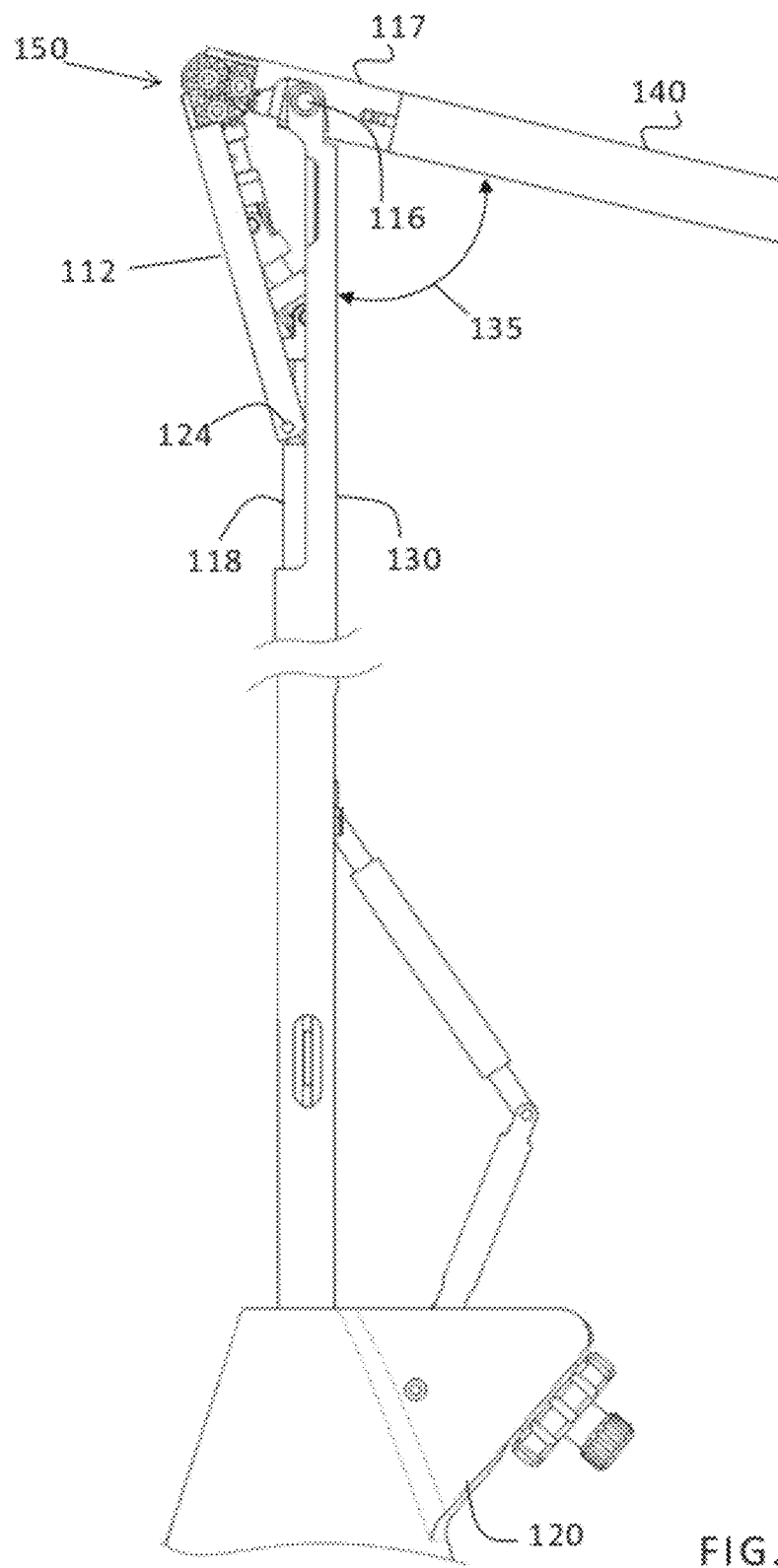

Referring now to the drawings, FIGS. 1A-1B illustrate an articulating surgical instrument 100 according to some exemplary embodiments of the invention. Instrument 100 is a surgical instrument, however, any medical instrument may be used in according with embodiments of the present invention. Instrument 100 includes a handle 110, an optional adaptor 120, a substantially straight proximal segment 130 and a substantially straight distal segment 140.

FIG. 1A illustrates instrument 100 in a straight configuration where proximal segment 130 and distal segment 140 form a substantially straight line. FIG. 1B illustrates an articulated configuration in which distal segment 130 is bent towards proximal segment 140 around a hinge 116, which is for example a pivot or a planar hinge. In the articulated configuration an articulation angle 135 of less than 180° is formed between distal segment 140 and proximal segment 130. According to embodiments of the present invention, articulation angle may be any angle between 1°-179°, for example an angle between 45°-179° such as 8°, 60°, 90°, 120° or any intermediate number.

Optionally, a medical tool is attached to an end 142 of distal segment 140, for example forceps or scissors. Alternatively or additionally, a medical tool or surgical instruments are contained within segment 140, for example a needle and/or screws, tacks or anchors. Optionally, a conduit is inserted through segment 130 and segment 140 for example for injecting medication or collecting of tissue samples. Optionally, mechanisms for actuating, dispensing and/or deploying a surgical instrument are also contained within segment 140.

Instrument 100 preferably comprises an articulating mechanism for articulating distal segment 140 towards (and away from) segment 130 and a drive mechanism for actuating the medical tool. The articulation and drive mechanism are operated from handle 110 or from optional adaptor 120 as will be further described with respect to FIGS. 11 and 12 below. Elements of the articulation and drive mechanism pass through proximal segment 130 which optionally consists of a plurality of layers, for example 2, 3, 4 or more layers.

Figure 1C:
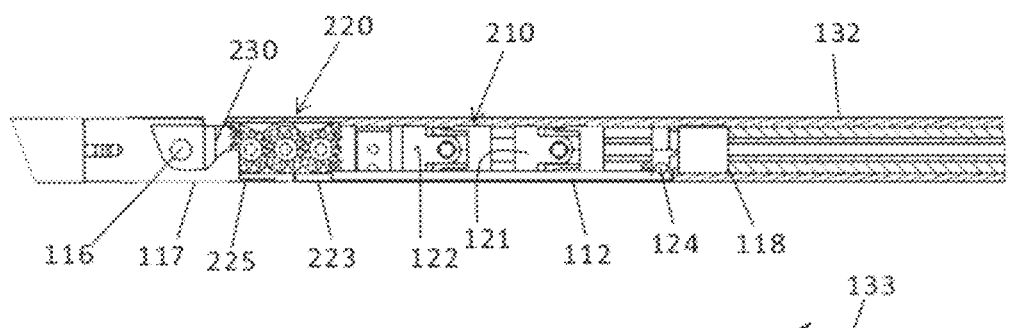
Figure 1D:
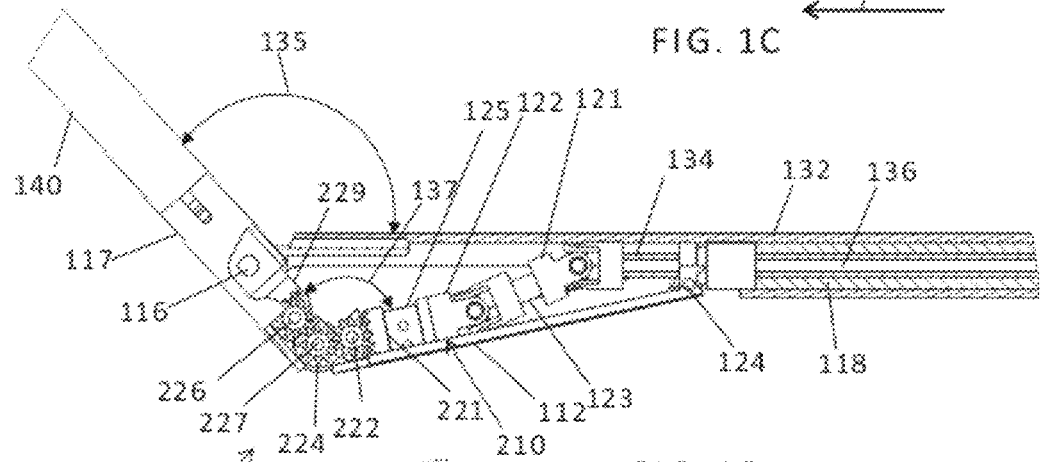
Figure 1E:
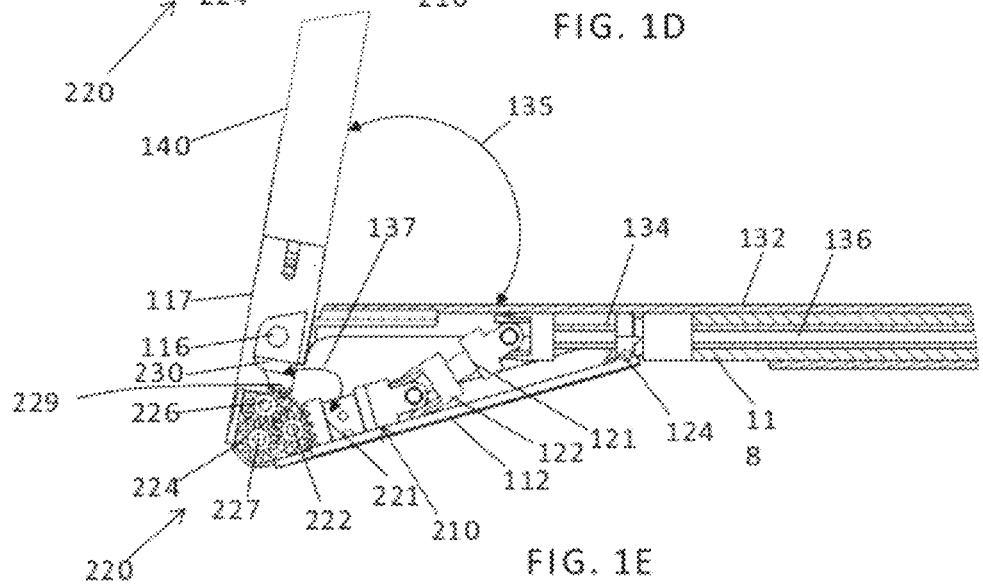

FIGS. 1C-1E are more detailed, partially cross-sectional views of the drive mechanism and lever of instrument 100 in the straight configuration (FIG. 1C) and in two different articulation configurations (FIGS. 1D and 1E). The layers of segment 130 will be described with reference to the cross-sectional views. Any of the layers may surround less than the entire circumference of the segment, for example, any of the layers may surround the entire 360° of the circumference or as less as only 30° of the circumference of segment 130.

An outer layer of proximal segment 130 will be referred herein as housing 132. Housing 132 optionally does not surround entire segment 132, for example as shown in FIG. 1C, the outer layer of segment 130 comprises of housing 132 and partial housings 112, 223 and 225.

An articulation mechanism is provided for articulating distal segment 140 towards or away from proximal segment 130. In the embodiments of FIG. 1, the articulation mechanism is a lever mechanism which articulates distal segment 140 around hinge 116. The lever mechanism consists of partial housing 112 that acts as a lever for controlling and/or stabilizing articulation of distal segment 140, as shown in FIGS. 1D and 1E. Lever 112 is attached by a lever hinge 124 to a drive element 118. Drive element 118 is a hollow tube which is driven from handle 110 or adaptor 120 in a direction 133 and thereby slides lever 112 distally and articulates distal segment 140 around hinge 116, forming articulation angle 135. Drive element 118 is positioned within (or partially within) housing 132 and constitutes a second layer of segment 130.

A drive mechanism is further provided for actuating a medical tool at (or in) distal segment 140. Optionally (and as shown), the drive mechanism transfers rotary motion to a medical tool. Alternatively or additionally, the drive mechanism transfers linear movement to the medical tool or to an actuator that controls the medical tool. The drive mechanism does optionally not follow substantially straight lines between the proximal and distal segment at the apex of articulation angle 135, but forms an angle 137 which is smaller than articulation angle 135.

Drive mechanism 150 includes a proximal shaft 210, a gear mechanism 220 and a distal shaft 230. In the straight configuration, proximal shaft 210 and distal shaft 230 are positioned within (or parallel to) proximal segment 130 and constitute a third layer of segment 130. In the articulated configuration, proximal shaft 210 extends from beneath proximal segment 130 and distal shaft 230 is positioned continuous to straight distal segment 140. Proximal shaft 210 is partially positioned in housing 112. Distal shaft 230 may partially be positioned in a housing 117 which extends from segment 140.

Proximal shaft 210 is connected by a link 121 to an inner tube drive 134 which is also part of the third layer of segment 130. In the articulated configuration, shaft 210 extends axially out of segment 130, requiring compensation the distance at the point of attachment of shaft 210 to inner tube drive 134. An exemplary distance compensation mechanism is shown and detailed with respect to FIG. 10 below. Additional links may be provided in proximal shaft for increasing flexibility of shaft 210, for example, link 122 is provided attaching a first rod 123 of shaft 210 with a second rod 125 (shown in FIG. 1D), such that rods 123 and 125 are articulated.

Gear mechanism 220 consists of face gears 221 and 229, attached to proximal shaft 210 and distal shaft 230 respectively. Gears 222, 224 and 226 are provided between face gears 221 and 229. Although three gears are shown, any number of wheels can be used in accordance with embodiments of the present invention, for example 1, 2 or 4 gears. By rotation of tube 134 (from handle 110 or adaptor 120), torque is transferred through link 121 (and optional links 122) to shaft 210 which causes face gear 221 to rotate and rotates gears 222, 224 and 226 to face gear 229, thereby rotating distal shaft 230.

Supports 223 and 225 are optionally provided for holding gears 222, 224 and 226 respectively, while allowing rotation of the gears. Supports 223 and 225 are interconnected by a hinge 227 which defines an additional axis around which gear mechanism 220 can rotate, thereby allowing shaft 230 to bend towards shaft 210 in the articulated configuration of instrument 100.

During articulation, gear 226 rotates around hinge 227 and around gear 224. Rotation around gear 224, may cause face gear 229 to rotate, thereby transferring undesired rotary motion to segment 140. In some embodiments, this undesired rotary motion is disabled by the addition of a coupler that separates face gear 221 from gear 222 during articulation. By this separation, the articulation of gear 226 around hinge 227 causes rotation of gears 224 and 222 rather than rotation of face gear 229 and segment 140.

Figure 1H:
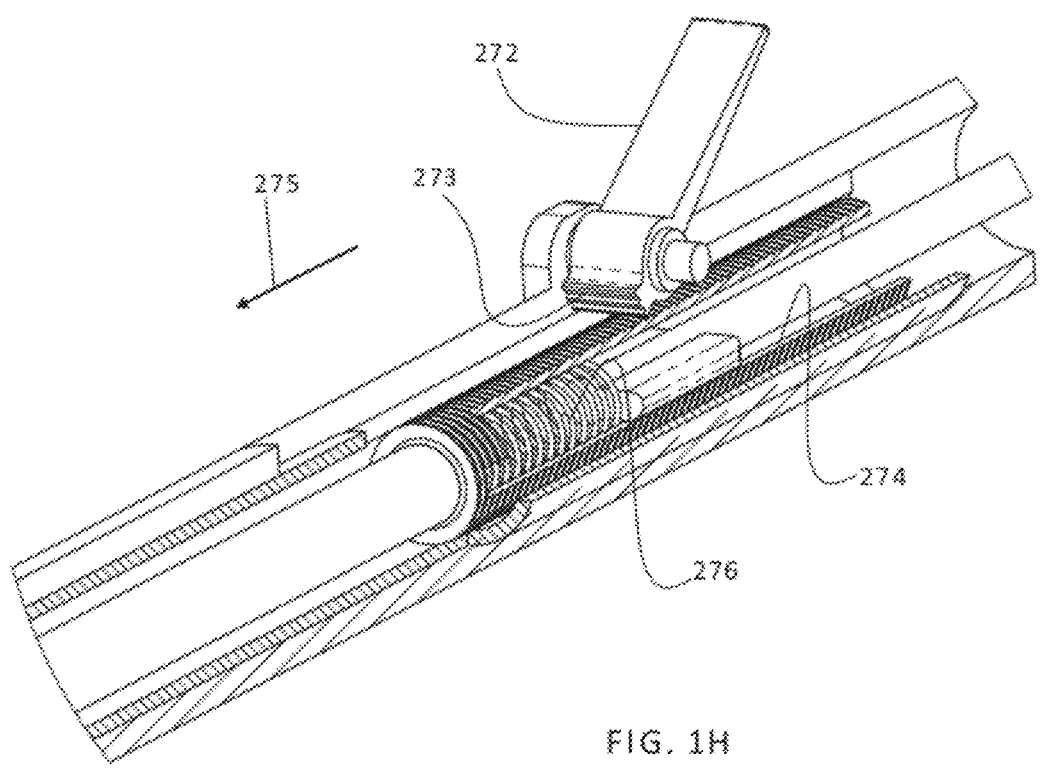

FIGS. 1F-1H illustrate a coupler 270 for separating face gear 221 from gear 222. FIG. 1F illustrates coupler 270 activated, where face gear is joined to gear 222 and FIG. 1G illustrates coupler 270 deactivated, where face gear 221 is separated from gear 222 and reveals a rod 231 between face gear 221 and gear 222. FIG. 1H is a closer view of coupler 270. Tube 134 includes at its end a spring which is surrounded by a helical tube 274. A handle 276 is provided for actuating coupler 270. Handle 270 includes teeth 273 at the inner side, facing helical tube 274. By pushing handle 270 in the direction 275 (i.e. from the position shown in FIG. 1F to the position shown in FIG. 1G), teeth 273 are inserted into helical tube 273 and pull tube 134 such that facial gear 221 separates from gear 222 and reveals rod 231.

Handle 272 is positioned as shown in FIG. 1F before or after articulation is performed and is positioned in the position shown in FIG. 1G during articulation. Coupler 270 is preferably positioned at the end of segment 130 and is not inserted into a body tissue. In some embodiments, coupler 270 is integrated in the mechanism which is activating the lever.

At least one wire or cable 136 may further be provided, passing through drive mechanism 150 and constituting a fourth layer of segment 130. Wire 136 is optionally an additional drive mechanism adapted to transfer linear motion to the medical tool or to an actuator of the medical tool. Optionally, wire 136 is pushed or pulled from handle 110 or adaptor 120.

Figure 2A:
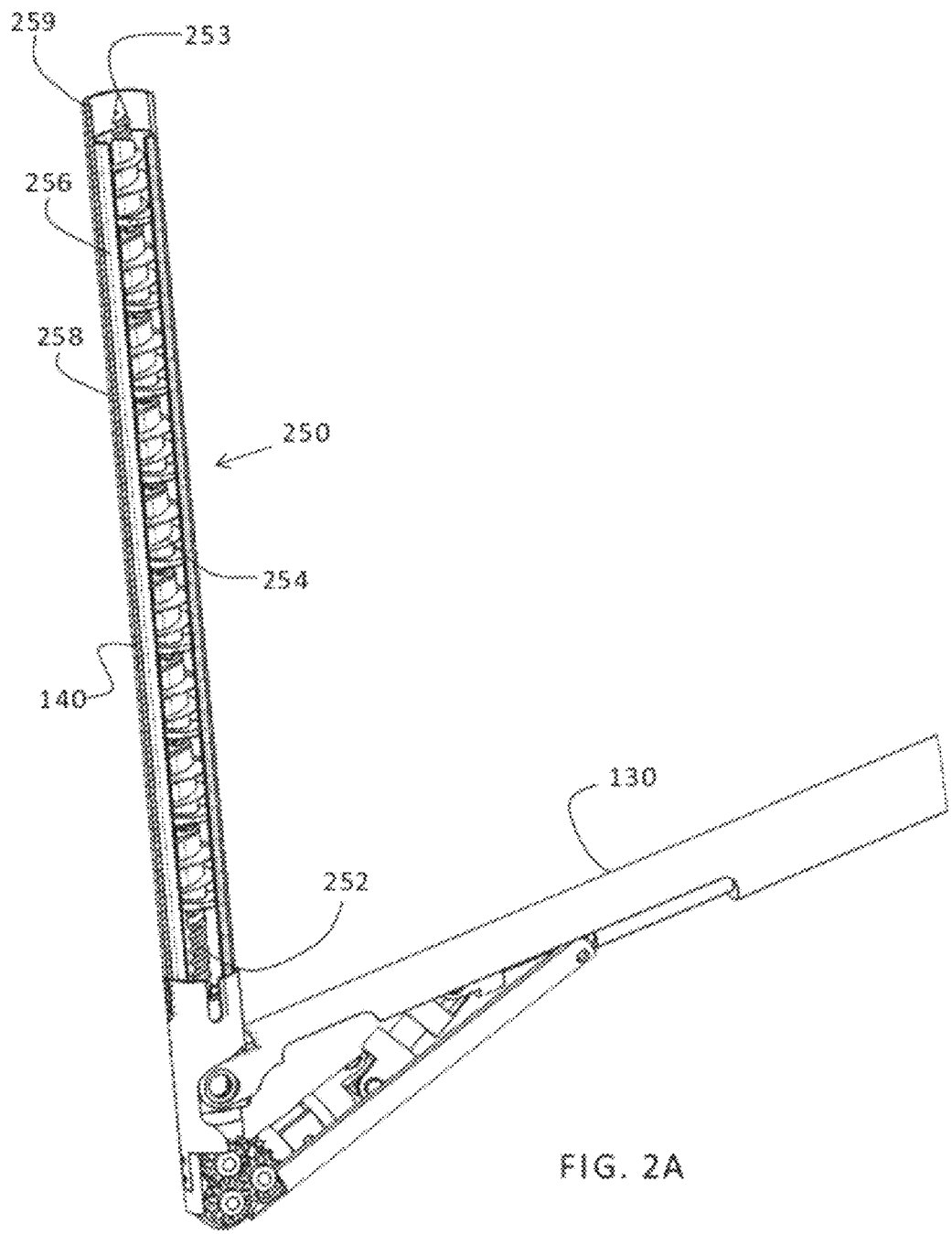
FIGS. 2A and 2B are partially cross-sectional illustrations of a medical tool actuated with the instrument in the embodiment illustrated in FIG. 1.
Figure 2B:
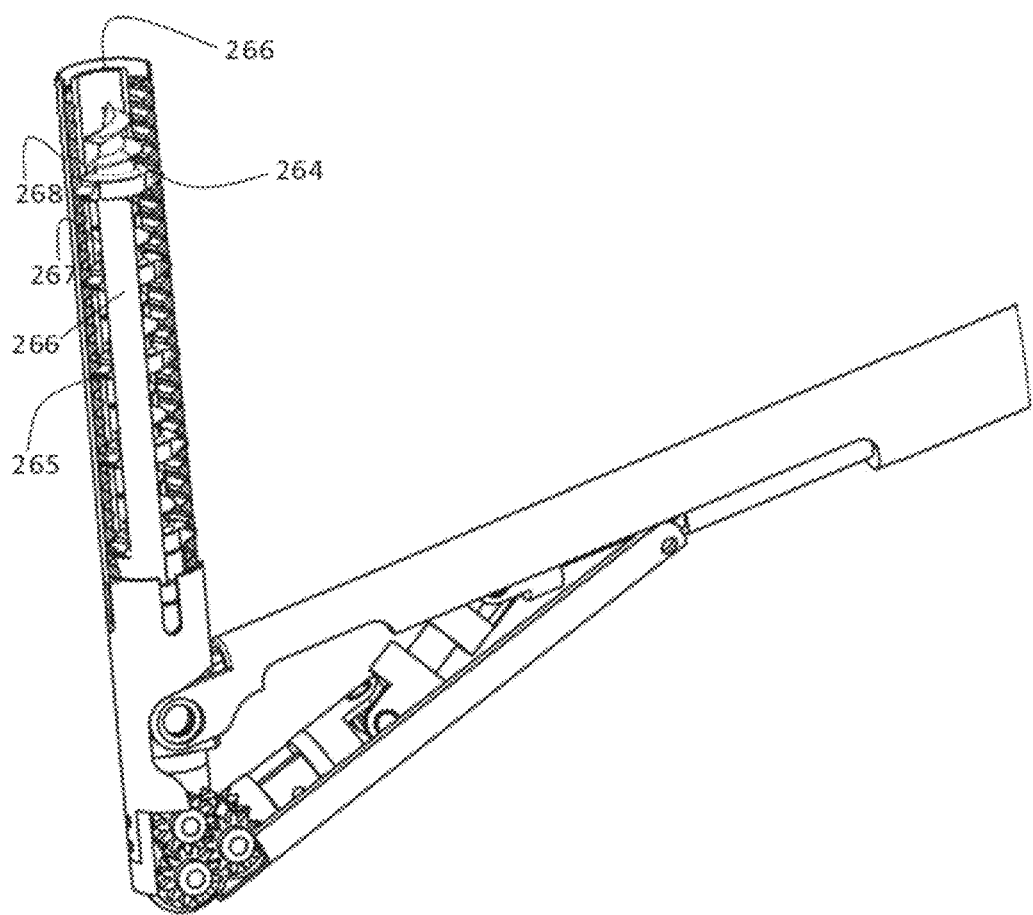

FIGS. 2A and 2B are cross sectional views of exemplary medical tools actuated by an instrument according to some embodiments of the invention. FIGS. 2A and 2B illustrate the instrument shown in FIGS. 1A-1F, it is understood that the medical tools may be actuated in accordance with any exemplary embodiment of the invention.

FIG. 2A illustrates a tacker 250 positioned within distal segment 140. Tacker 250 includes a long threaded element 252, having a needle point 253, and a number of helical fasteners 254 threaded around element 252. A plurality of fasteners may be loaded in accordance with embodiments of the invention, for example between 1-10 fasteners and deployed as desired. Element 252 and fasteners 254 are positioned within an internally threaded sleeve 256 which is positioned in an outer layer 258 of segment 140. Optionally, needle point 253 is positioned out of sleeve 256.

In order to fasten fasteners 254 in a body, needle point 253 is stabbed in a body tissue and fasteners 254 are then rotated by sleeve 256 till they exit from threaded element 252 and are fastened within the body tissue. In some embodiments, element 252 does not advance but remains static and segment 140 withdraws. A retraction spring 259 may be provided at segment 140, where needle end 253 is positioned. By forcing segment 140 on to a body tissue, retraction spring 259 contracts, thereby revealing needle end 253. Optionally, retraction spring 259 is positioned at the end of segment 140 as shown in FIG. 2A. Alternatively, retraction spring 259 is positioned at any other position of segment 140. Any retraction spring known in the art can be used in accordance with embodiments of the present invention. Optionally, a collapsible element which provides a controlled threshold force is used as a retraction spring, in order to prevent undesired exposure of end 253. In these embodiments, element 252 is static and does not move during actuation of tacker 250.

In an alternative embodiment, retraction spring 259 is not present and element 252 moves in linear direction, for example by a spring provided at the end of the needle, opposite to end 253. Element 252 is controlled from handle 110 or adaptor 120. Element 252 can optionally freely move linearly during articulation of distal segment 140 but should only controllably move in the linear direction after articulation is completed in order to stab the needle in a body tissue. A distance compensation mechanism for element 252 is detailed with respect to FIGS. 8 and 9 below.

FIG. 2B illustrates an alternative tacker to be actuated in accordance with an exemplary embodiment of the invention. A tacker 260 is shown contained within distal segment 140. Tacker 260 includes a number of helical fasteners 264 inside an internally threaded tube 266. Tube 266 has a number, for example 2, longitudinal slits through which wings 265 of fasteners 264 extend. Tube 266 is shown cut off at the end of segment 140 for clarity but covers all of fasteners 264. Fasteners 264 are held by wings 265 in threads 268 of segment 140. By transfer of rotary movement through the drive mechanism, tube 266 is rotated, thereby advancing fasteners towards the end of segment 140 and then screwed in a body tissue. In the embodiment shown in FIG. 2B, no linear movement mechanism is required.

Figure 3A:
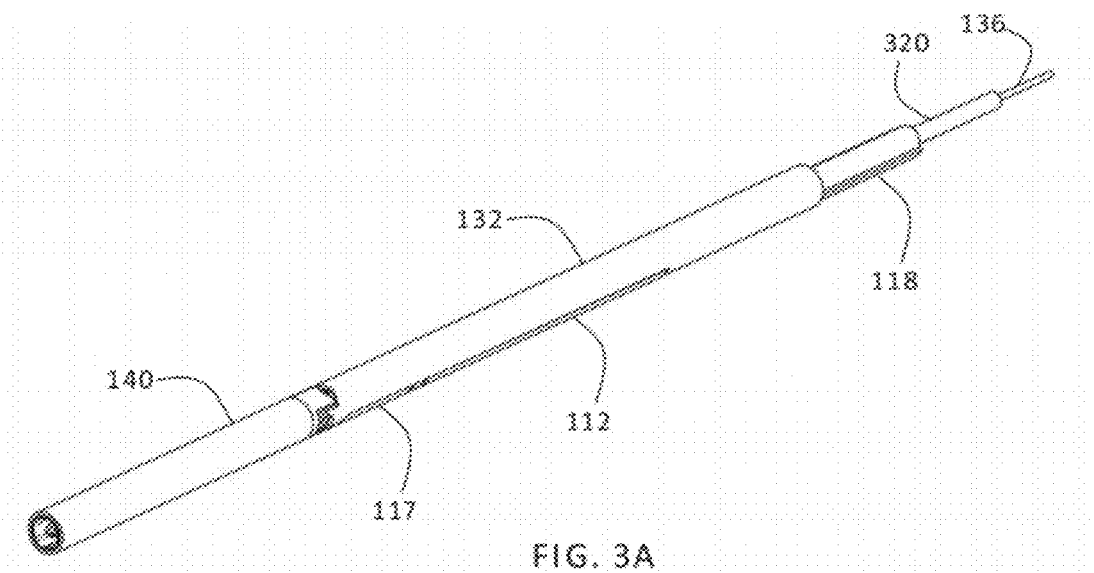
FIGS. 3A and 3B are schematic illustrations of an articulation and drive mechanism useful in an articulated surgical instrument similar to that of FIG. 1, in accordance with another embodiment of the invention.
Figure 3B:
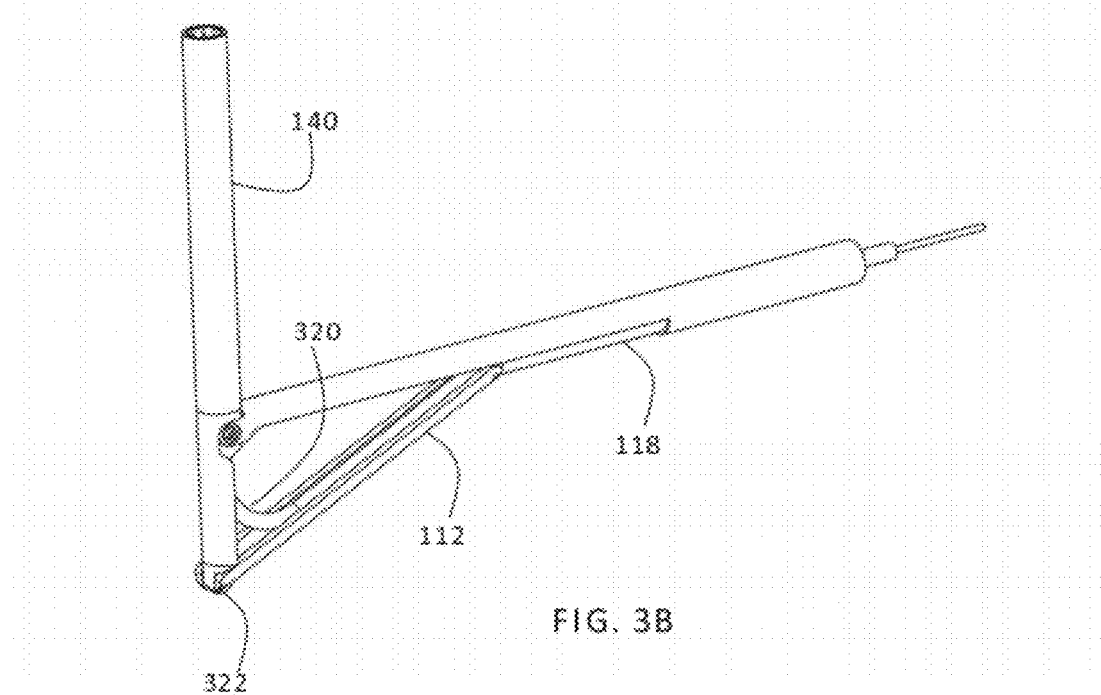

FIGS. 3A and 3B illustrate a drive mechanism in accordance with another embodiment of the invention. FIG. 3A shows a straight configuration in which sliding lever 112, housing 117 and a drive mechanism 320 are positioned parallel to proximal shaft 130. In the articulated configuration shown in FIG. 3B, drive mechanism 320 is positioned partially within lever 112 and housing 117. Drive mechanism 320 replaces shafts 210 and 230 and drive mechanism 220 in the embodiment shown in FIG. 1.

Drive mechanism 320 is a flexible shaft, generally positioned within a canella in a sheath, which is positioned within segments 130 and 140 in the straight configuration and is attached to a medical tool at or in segment 140. Shaft 320 is preferably controllable from handle 110. In the straight configuration, shaft 320 follows the shape of (and is positioned within) substantially straight segment 130. In the articulated configuration, drive mechanism 320 extends from a joint 322 connecting lever 112 and housing 117 and is not wholly positioned within lever 112 and housing 117, as shown in FIG. 3B.

Rotation of shaft 320 from handle 110 transfers torque through the instrument, thereby rotating medical tool at or in segment 140. In some embodiments, shaft 320 is hollow and other drive mechanisms can be passed through hollow shaft 320. For example, as shown in FIGS. 3A and 3B, a wire 136 is positioned within hollow shaft 320. It is understood that more than one wire 136 can be passed through shaft 320, for example two or more wires.

In some embodiments of the invention, a conduit is passed through shaft 320 for injection of medication in a body tissue. Alternatively or additionally, tissue samples are collected through the conduit by for example applying a vacuum suction.

Figure 4A:
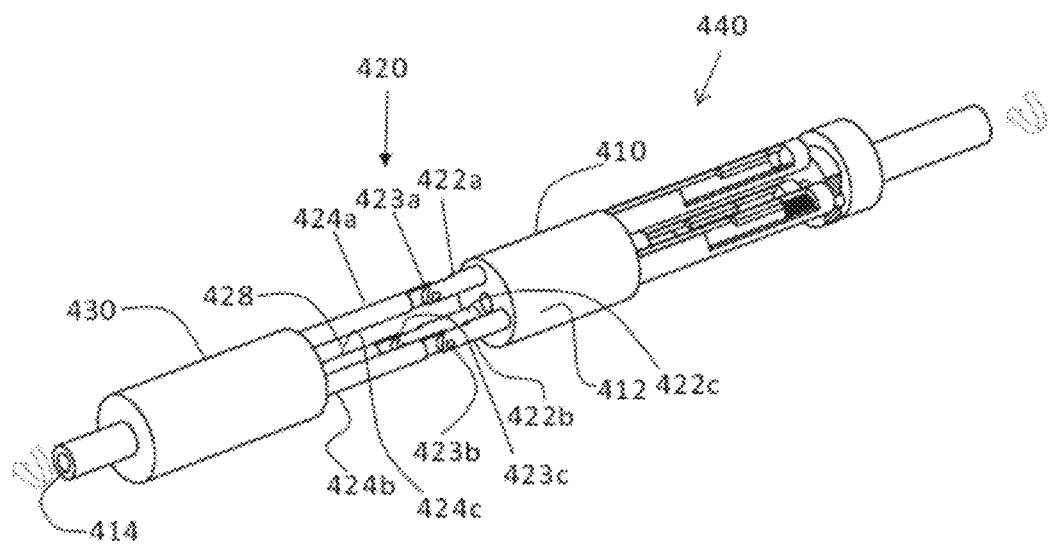
FIGS. 4A-4F are schematic illustrations of a drive mechanism in accordance with yet another embodiment of the invention.
Figure 4B:
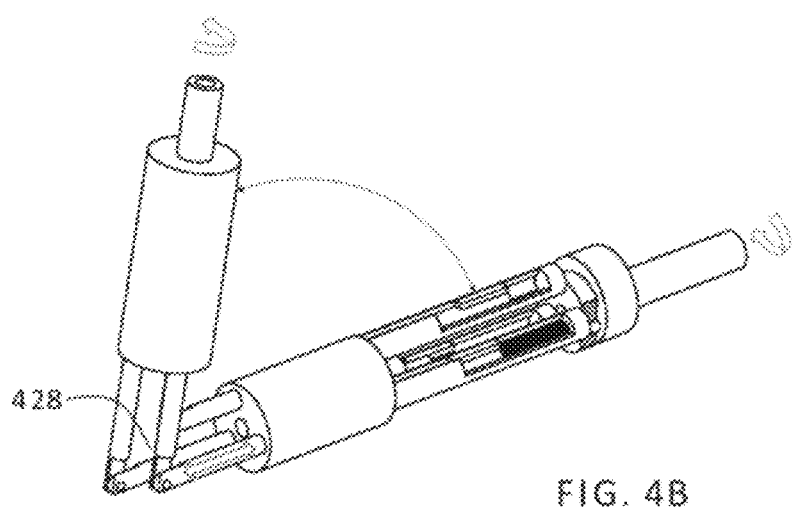
Figure 4C:
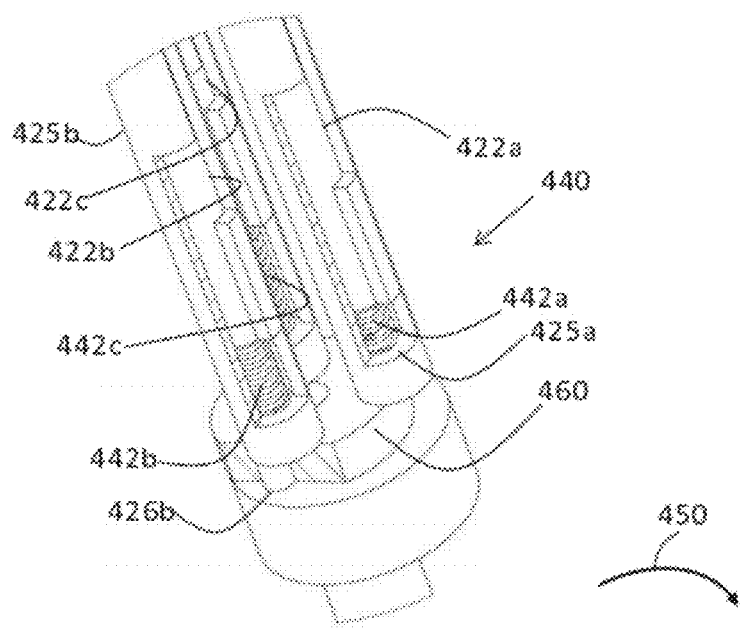
Figure 4D:
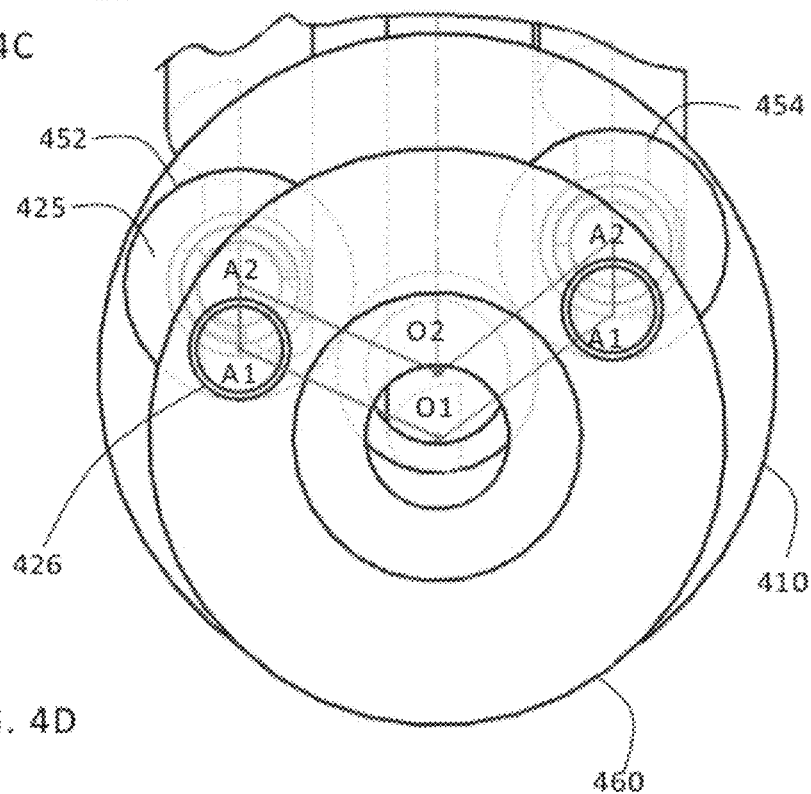
Figure 4E:
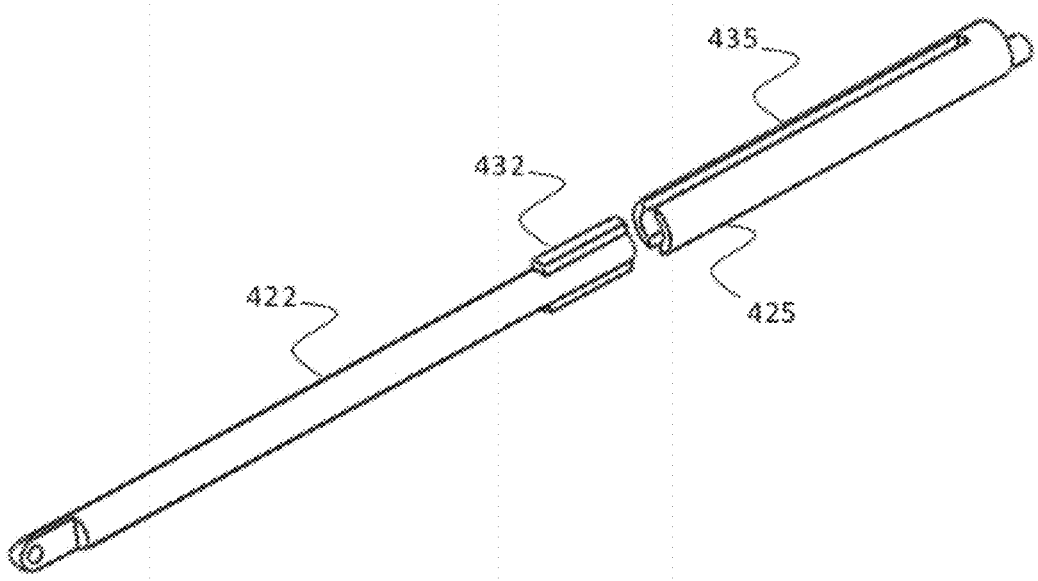
Figure 4F:
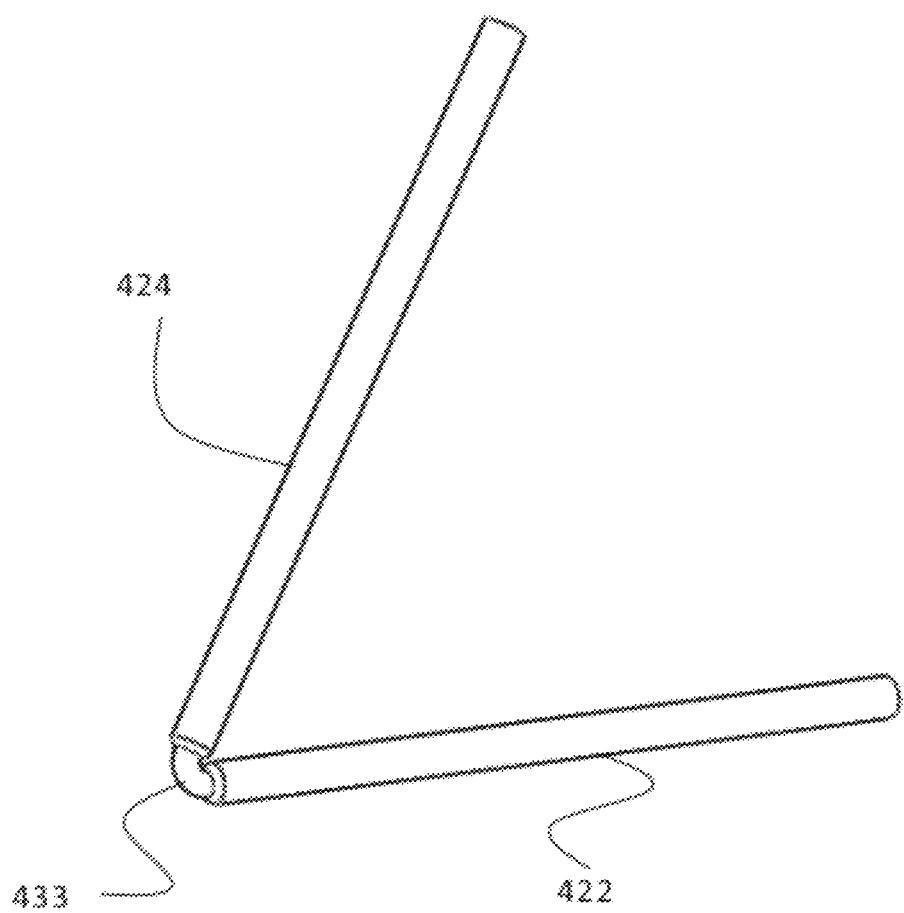

FIGS. 4A-4G illustrate a drive mechanism 420 in accordance with yet another embodiment of the invention. Drive mechanism 420 is shown situated between proximal shaft 410 and distal shaft 430. FIGS. 4A-4F illustrate the drive mechanism without a surrounding instrument. An exemplary surrounding instrument is shown in FIG. 4F and is similar to the instrument shown in FIGS. 1-3. Other instruments may be used in accordance with exemplary embodiments of the invention, for example instruments where the drive mechanism follows substantially straight lines between the proximal and distal segments at the apex of the articulation angle.

Drive mechanism 420 consists of three pairs of rods 422a and 424a, 422b and 424b and 422c and 424c, generally referred hereinafter as rod pairs 422 and 424. Rods 422a, 422b and 422c are connected to proximal shaft 410 and rods 424a, 424b and 424c are connected to distal shaft 430. Each pair of rods is interconnected by hinges 423a-c respectively. Hinges 423a-c are optionally planar hinges or joints which can articulate in one direction only.

Rotary motion is transferred from proximal shaft 410 through rod pairs 422 and 424 to distal shaft 430. Substantially any number of rod pairs 422 and 424 can be used for example 1, 2 or 4 rod pairs. Preferably, the rod pairs are spaced angularly equally apart from each other and are within the diameter of shafts 410 and 430. A passageway 428 situated between rod pairs 422 and 424 enables one or more additional drive mechanisms to be passed through central holes 412 and 414 of shafts 410 and 430 respectively, for example a linear movement mechanism such as a spring or wire.

Drive mechanism 420 can freely rotate in the straight configuration shown in FIG. 4A and in an articulated configuration, for example as shown in FIG. 4B. Since planar hinges 423a-c are used to connect rod pairs 422 and 424, the rods can articulate at two angles only and should be aligned such that the different rods will always articulate in the same direction.

An alignment mechanism 440 is optionally provided for keeping rod pairs 422 and 424 aligned in the straight and articulated configuration. FIG. 4C is a closer view of alignment mechanism 440. Alignment mechanism 440 is shown attached to proximal shaft 410 but could be attached to distal shaft 430 in accordance with exemplary embodiments of the invention.

Rods 422a-c are partially contained in housings 425a-c respectively. FIG. 4E is a closer view of an exemplary rod 422 and housing 425. Rods 422 include extensions 432 which fit in longitudinal slots 435 of housing 425, thereby preventing rods 422 from rotating with respect to housings 425.

Housings 452a-c include axles 426a-c at their ends which are received in a disk 460. Axles 426a-c are eccentric of the axes of housings 426a-c (and this of rods 422) and disk 460 is positioned eccentric to shaft 410. Preferably, axles 426a-c are eccentric by the same amount and in the same direction as disk 460. The eccentric positions of axles 426a-c and disk 460 assure that housings 426a-c will not rotate around their axis during rotation of disk 460.

FIG. 4D illustrates the rotation of disk 460 with an exemplary housing 425. A1 indicates the center of knob 426 and A2 indicates the center of housing 425 and a rod 422. O1 indicates the center of disk 460 and O2 indicates the center of shaft 410. The distance between A1 and A2 equals the distance between O1 and O2. During rotation of disk 460 in the direction 450, housing 425 (and knob 426) move from a position 452 to a position 454. During rotation, the distance between A1 and A2 remains equal to the distance between O1 and O2, thereby preventing rotation of housing 425 around its axis.

An additional alignment requirement is a linear alignment, preventing rod pairs 422 and 424 to move in a linear direction so that the joints will always be positioned on the same axis. A spring 442a-c is provided between each rod 422a-c and the end of housing 425a-c for controlling linear movement of the rods. The rods are able to slide within their respective housings to change the length of the rod/housing configuration as required.

In accordance with another embodiment of the invention, rod pairs 422 and 424 are interconnected by a flexible element 433, which can bend at any direction, for example as shown in FIG. 4F. The use of flexible element eliminates the use of alignment mechanism 440 since the rod pairs can bend around any axis. Flexible element 433 is preferably not stretchable and may be made, for example, of nitinol or non-stretchable nylon. In some embodiments, a linear alignment mechanism, for example springs 442a-c, is provided for linear alignment of the rod pairs. However, housings surrounding the rods need not be slotted and the eccentricities described above are not generally provided.

Figure 4G:
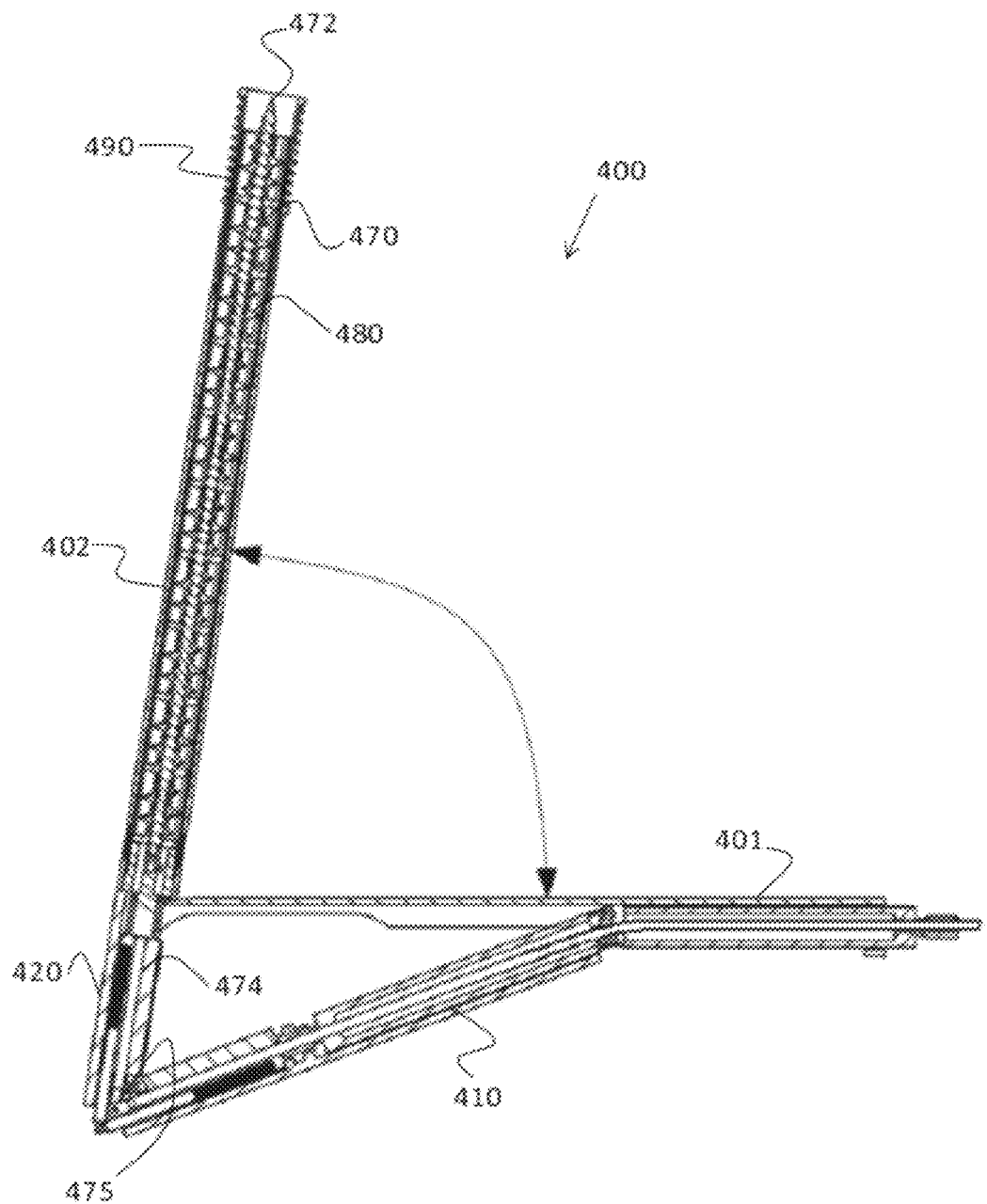
FIGS. 4G and 4H are partially cross-sectional illustrations of the drive mechanism of FIGS. 4A-4E in the instrument of FIGS. 1A and 1B.

FIG. 4G is a cross-sectional view of medical instrument 400 with a drive mechanism 420 as shown in FIGS. 4A-4F. Medical instrument 400 is similar to instrument 100 shown in FIG. 1, except for the drive mechanism. Distal segment 402 and proximal segment 401 are shown. A tacker, similar to the tacker shown in FIG. 2A, is positioned within distal segment 402. The tacker consists of a threaded shaft 470 and screws 480. In the embodiment shown in FIG. 4G, shaft 470 is static and a retraction spring 490 is provided at the end of segment 402, where a needle end 472 is positioned. Thus, by forcing segment 402 on to a body tissue, retraction spring 490 contracts, thereby revealing needle end 472.

In order to keep shaft 470 static, a tube 474 is provided through drive mechanism 420, supporting shaft 470. Tube 474 optionally also has a joint 475 allowing tube 474 to bend with rod pairs 422 and 424. Alternatively, tube 474 is relatively flexible such that it can bend and follow the articulation of drive mechanism 420.

Optionally, shafts 470 and 474 are replaced by a conduit for collecting tissue samples and/or injection of medication.

Figure 4H:
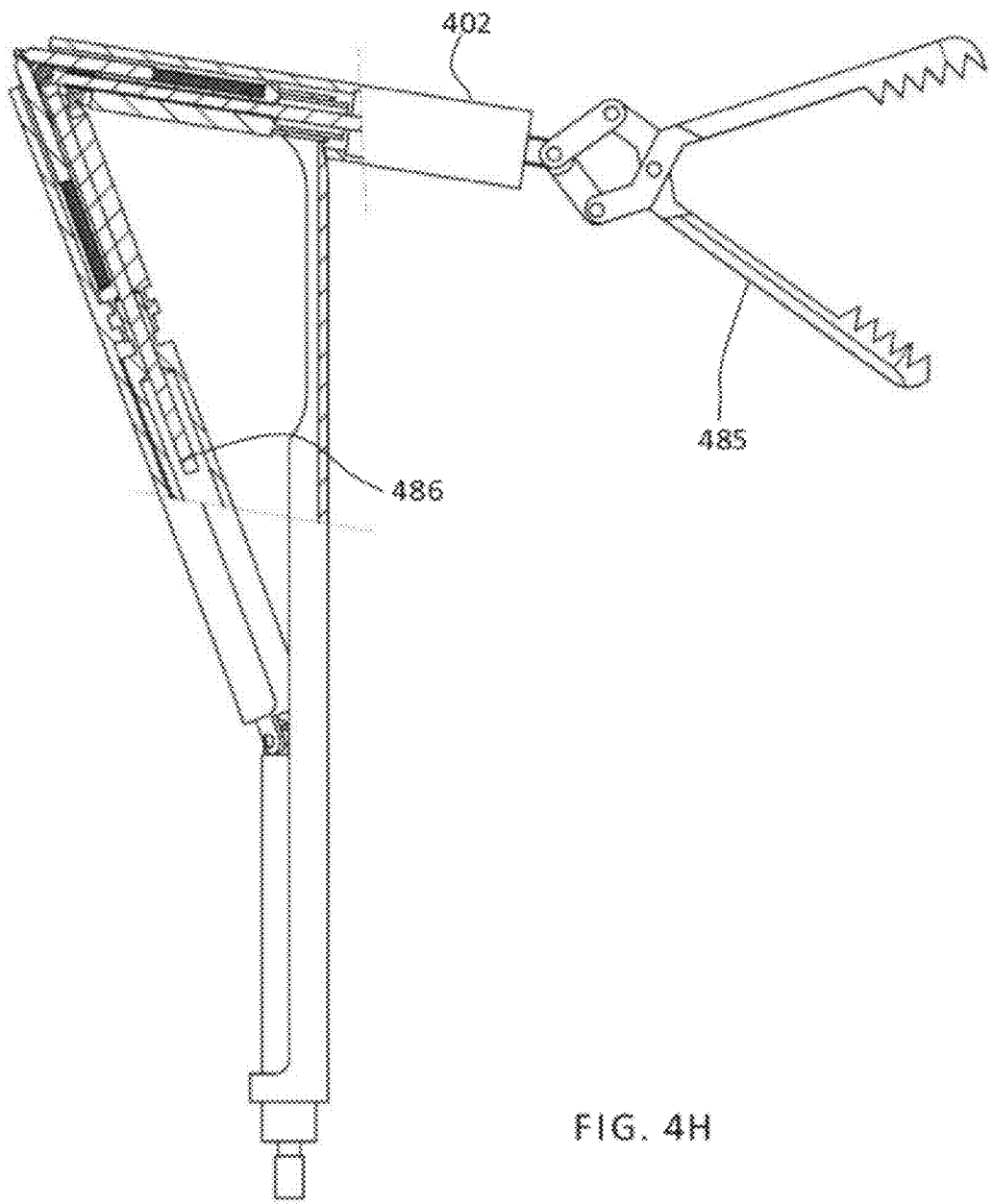

FIG. 4H illustrates an instrument similar to the instrument shown in FIG. 4G, where forceps 485 are provided at the end of distal segment. The forceps are actuated by a cable 486 that passes through central holes 412 and 414 of the drive mechanism. The rotation provides for changing the aspect of the forceps.

A number of drive and articulation mechanisms for instrument 100 are provided in accordance with embodiments of the present invention. In general, the drive and articulation mechanisms can be separated into two groups. A first group in which the drive mechanism and lever are positioned exterior of the articulation angle, for example as shown in FIGS. 1-4 and described above. In this group, the lever is pushed in order to articulate the distal segment towards the proximal segment. A second group of a drive mechanism and lever which are positioned interior of the articulation angle, for example as shown in FIGS. 5 and 7 and described below. In the second group, the lever is pulled in order to articulate the distal segment towards the proximal segment. In both groups, the drive mechanism does not follow the articulation angle and is not substantially affected by forces involved in articulating and maintaining an articulated configuration of the instrument.

A detailed description of the second group is now provided with reference to FIGS. 5-7.

Figure 5A:
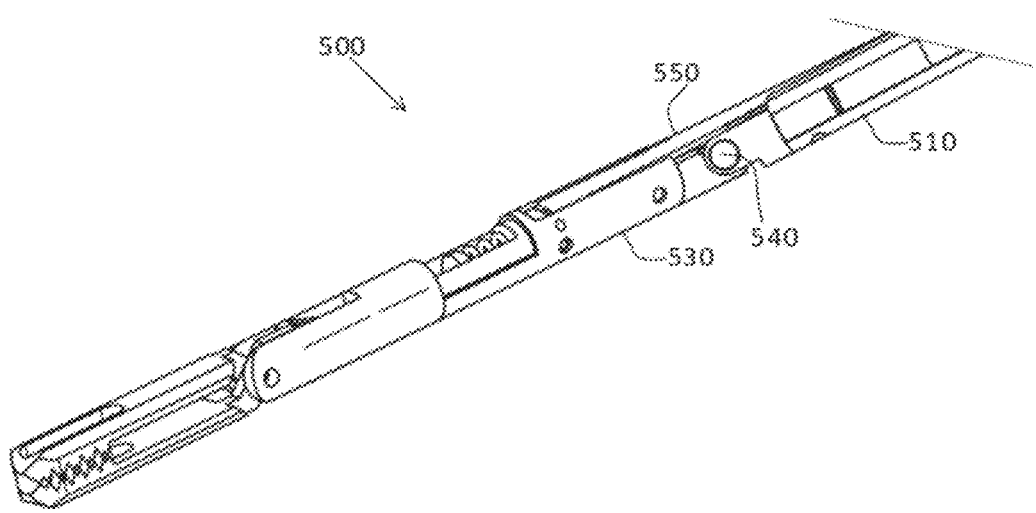
FIGS. 5A-5E are schematic illustrations of an articulation and drive mechanism useful in an articulated surgical instrument in accordance with another embodiment of the invention.
Figure 5B:
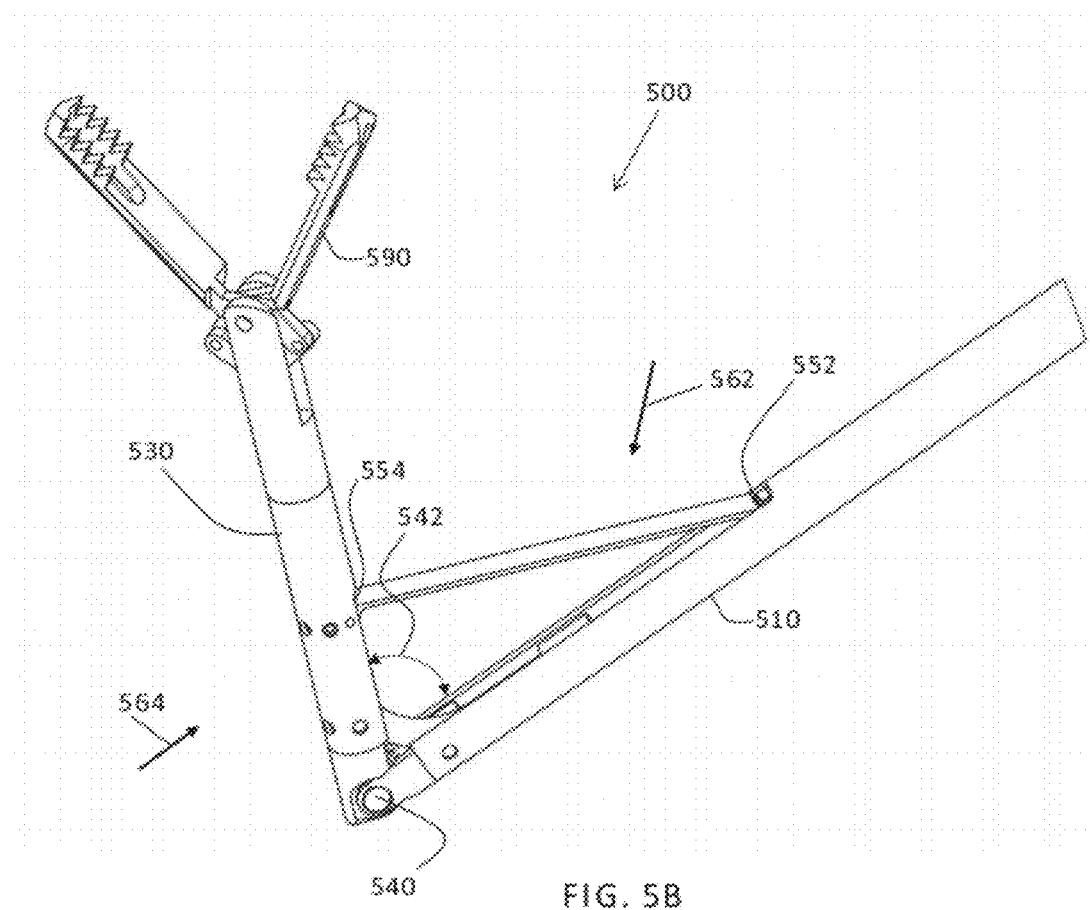
Figure 5C:
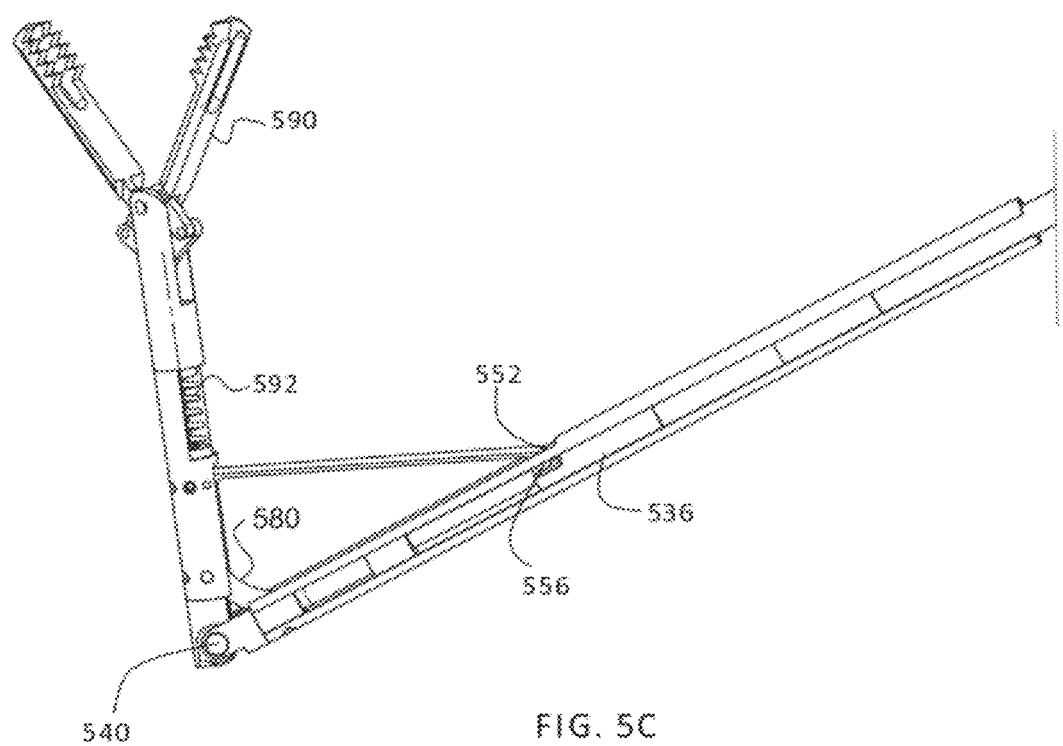

FIGS. 5A-5C illustrate a drive and articulation mechanism 500 in accordance with another embodiment of the invention. FIG. 5A illustrates a straight configuration and FIG. 5B illustrates an articulated configuration in which a substantially straight distal segment 530 is bendable towards a substantially straight proximal segment 510. An articulation angle 542 exists at the junction of segments 510 and 530 at a joint 540. Joint 540 can be any joint known in the art, for example a planar pivot. In some embodiments, no joint 540 is provided and articulation angle 542 is defined by (virtual) continuation of straight segments 510 and 530.

A lever 550 is provided for articulating segment 530 towards segment 510. Lever 550 is controlled from handle 110 or adaptor 120 shown in FIG. 1 and detailed with respect to FIGS. 11 and 12 below. A first end 552 of lever 550 is attached to proximal segment 510 and a second end 554 of lever 550 is attached to distal segment 530. In the straight configuration shown in FIG. 5A, lever 550 is positioned parallel to (or within) segments 510 and 530. In the articulated configurations shown in FIG. 5B, lever 550 is extended out of segments 510 and 530 and is positioned between segments 510 and 530, interior of articulation angle 542.

In order to extend out of segments 510 and 530, lever 550 should be slidably attached to the proximal segment, so as to allow for a distance change in the point of attachment to the segment. FIG. 5C is a cross-sectional view of the articulated configuration of FIG. 5B. FIG. 5C shows end 552 of lever 550 attached by a lever hinge 556 to drive element 536 which slides along a drive mechanism 580.

Drive mechanism 580 is a flexible shaft, generally positioned within a canella in a sheath, which is positioned within segments 510 and 530 in the straight configuration. In the articulated configuration, shaft 580 extends from segments 510 and 530 and is positioned between articulation angle 542 and lever 550. By extension of drive mechanism 580 out of joint 540, drive mechanism 580 is less affected by forces involved with articulating segments 510 and 530, for example forces indicated by arrows 562 and 564 forces 562 and 564 may also represent external forced applied when the surgical tool is forced to the patient body. In the articulated configuration, drive mechanism 580 is positioned within the articulation angle but does not pass through straight lines between the proximal and distal segment at the apex of angle 542. In the embodiment shown in FIG. 5, drive mechanism 580 does not pass through joint 540.

Shaft 580 is attached to a medical tool at the end of segment 530, for example forceps 590 as shown in FIGS. 5B and 5C. Shaft 580 is preferably controllable from handle 110 and optionally transfers rotary motion from segment 510 through segment 530 to rotate forceps 590. In some embodiments, shaft 580 is hollow and enables one or more additional drive mechanisms to pass therethrough such as wire or cable that transfers linear motion/force that closes the forceps against the force of spring 592. Alternatively or additionally, shaft 580 may transfer both rotary and linear motion from segment 510 through segment 530 to forceps 590. For example, as shown in FIG. 5C, a spring 592, part of the actuation mechanism, is provided in segment 530 for actuating forceps 590.

Figure 5D:
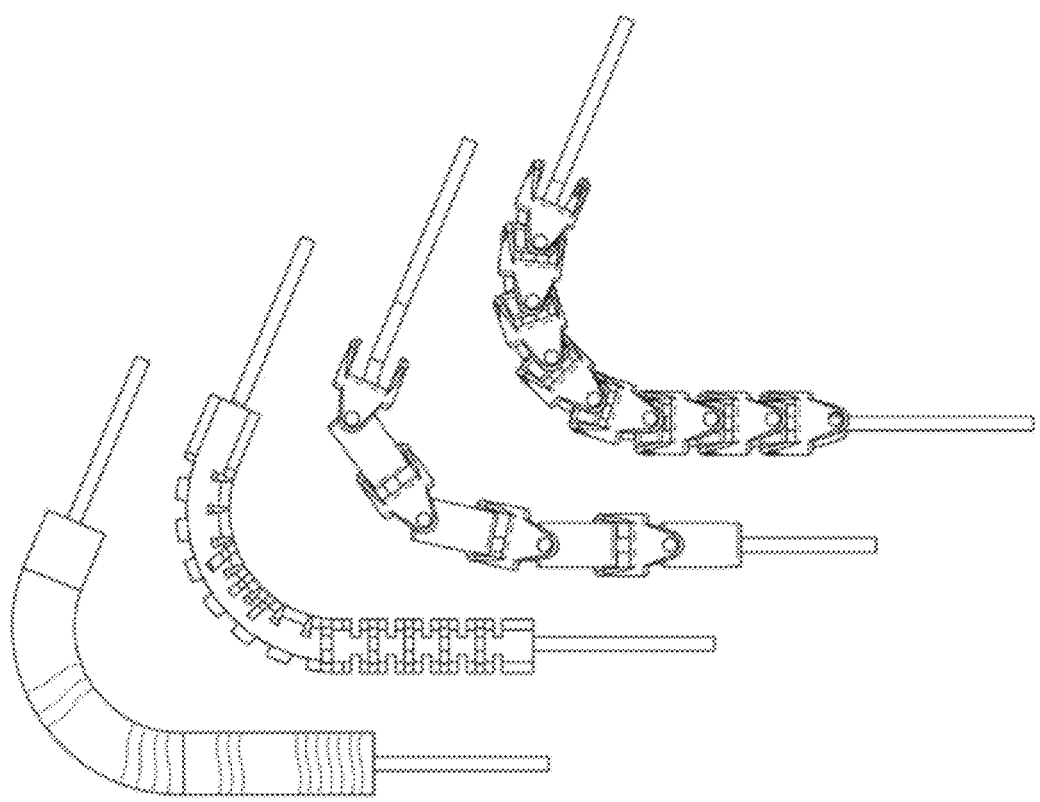

Shaft 580 may be any flexible shaft known in the art. FIG. 5D illustrates exemplary flexible shafts that can be used in accordance with exemplary embodiments of the present invention, for example a sheath or a plurality of interconnected links or joints. The shafts shown in FIG. 5D can also be used as replacements for shaft 320 shown in FIG. 3B.

Figure 5E:
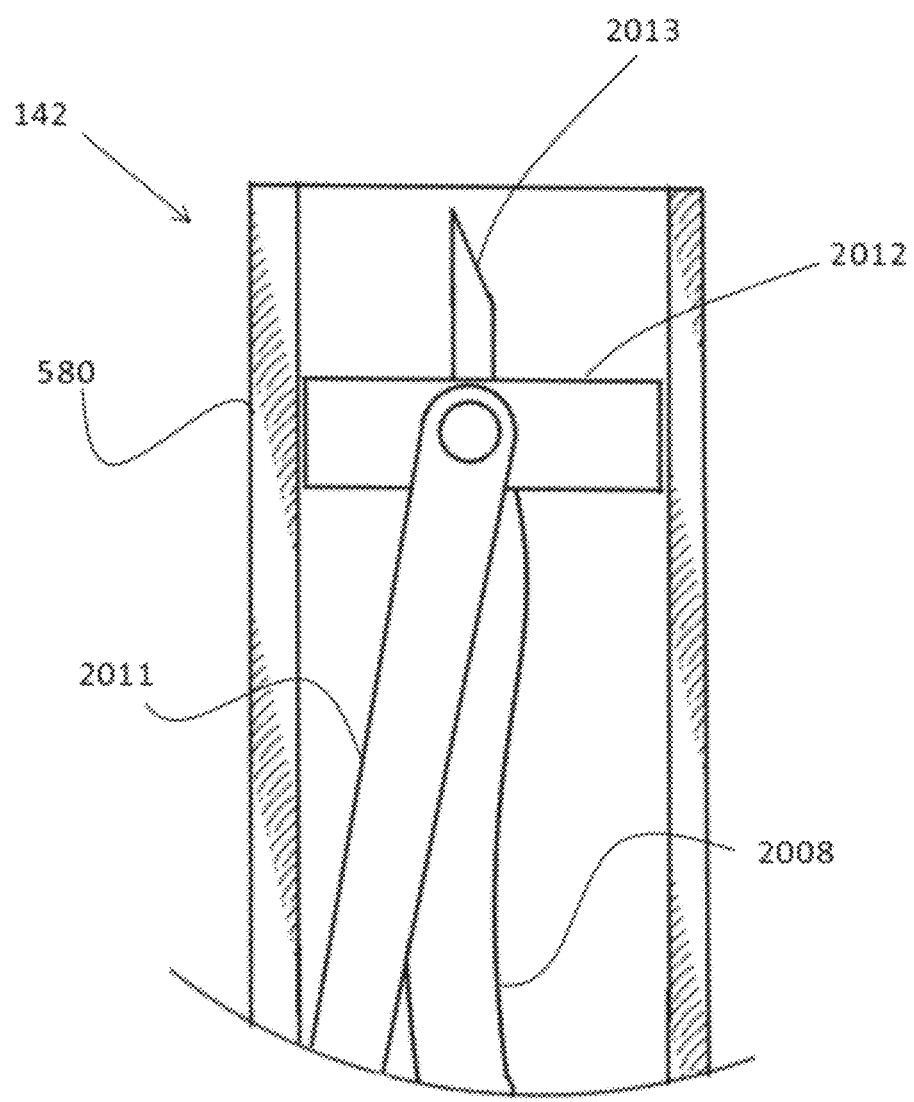

In some embodiments of the invention, shaft 580 is a flexible conduit through which medication or tissue samples are provided. FIG. 5E is a cross-sectional view of end 142 of distal segment 140 showing a syringe 2013 at the end of conduit 580. A needle support 2012 is provided attached by a lever 2011 to conduit 580. When shaft 580 lever 2011 is pushed, syringe 2013 is revealed and can be stabbed in a body tissue for injecting medication or collecting tissue samples.

Figure 6A:
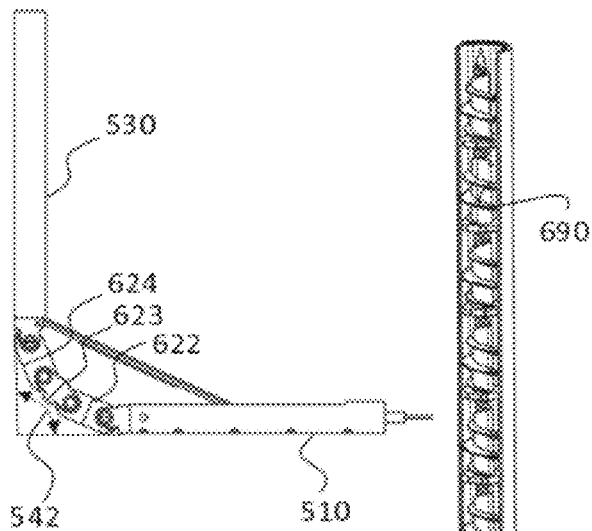
FIGS. 6A-6C are schematic illustrations of the articulation and drive mechanism of FIGS. 5A-5C, where the proximal and distal segments are connected by a flexible hinge in accordance with an exemplary embodiment of the invention.
Figure 6B:
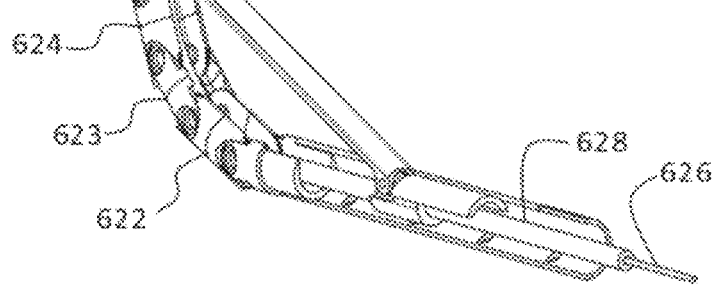

FIGS. 6A and 6B illustrate an exemplary embodiment of the invention where hinge 540 is replaced by three interconnected links 622, 623 and 624. In the embodiment shown in FIGS. 6A-B, no planar hinge 540 is provided for supporting articulation of segments 510 and 530. Articulation angle 542 is defined by continuing segments 510 and 530, as shown by dotted lines in FIG. 6A.

FIG. 6B is a partial cut away isometric view of the flexible hinge shown in FIG. 6A. A tacker 690 is provided within distal segment 530. A flexible shaft 628 is provided in segment 510 and through links 622 and 624 for transferring rotary motion. Optionally, at least one wire 626 is provided within shaft 628 for transferring linear motion. Optionally, wire 626 pulls back the central elongated needle and serves as a fixating mean of the central needle while the tackers are rotated around the central needle as detailed with respect to FIG. 2A. Alternatively, wire 626 is movable and dynamically actuates the needle of the tacker or any other medical tool, for example by pulling the wire.

Figure 6C:
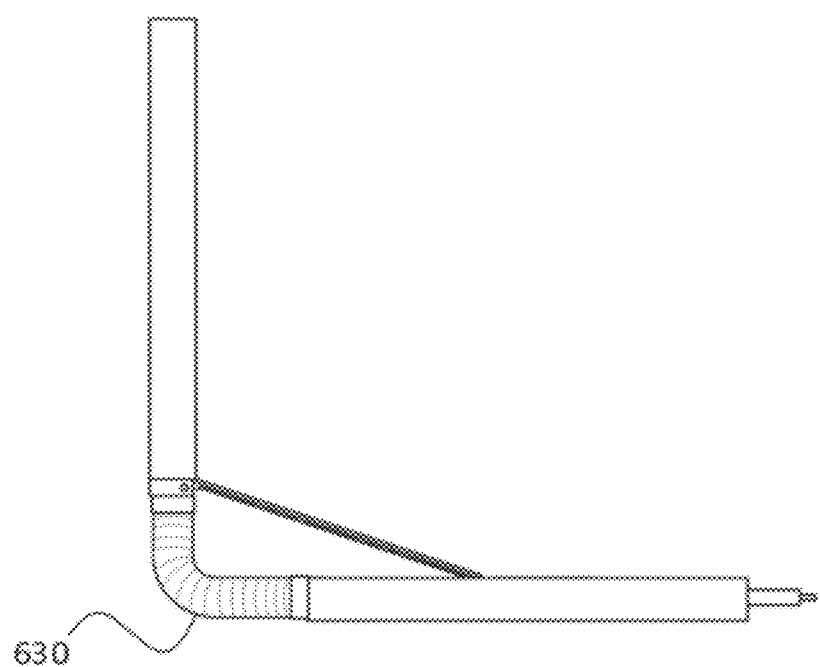

FIG. 6C illustrates an embodiment where links 622, 623 and 624 are replaced by a plurality of closely interconnected links 630.

Figure 7A:
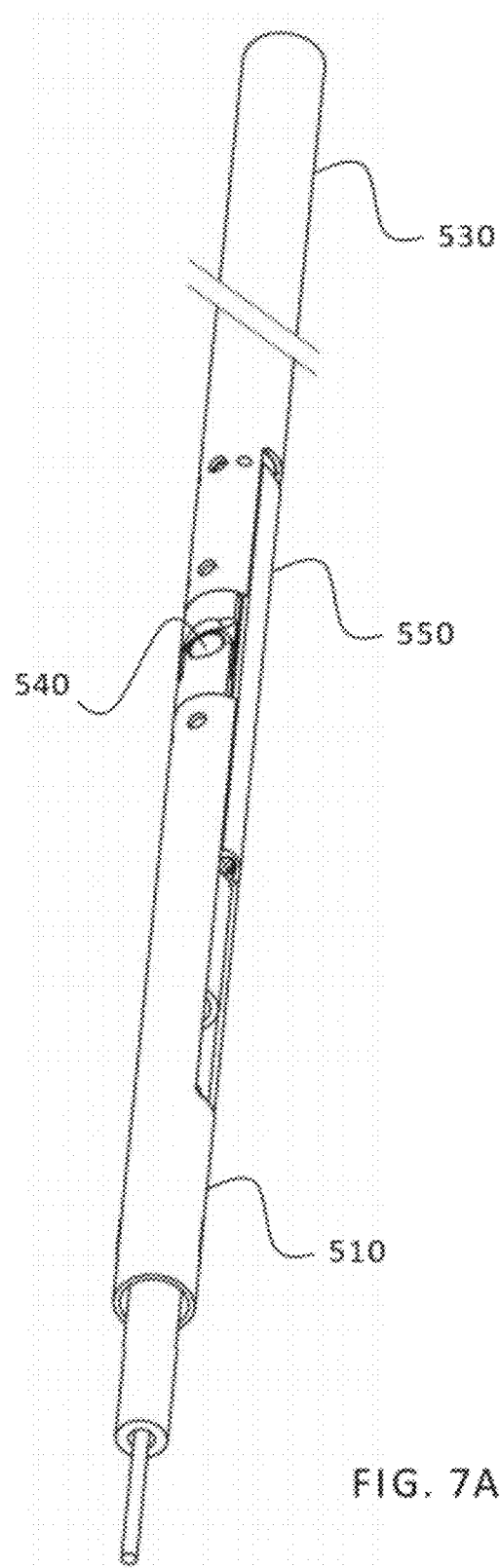
FIGS. 7A-7C are schematic illustrations of an articulation and drive mechanism of FIGS. 5A-5C using a rigid rod in accordance with another embodiment of the invention.
Figure 7B:
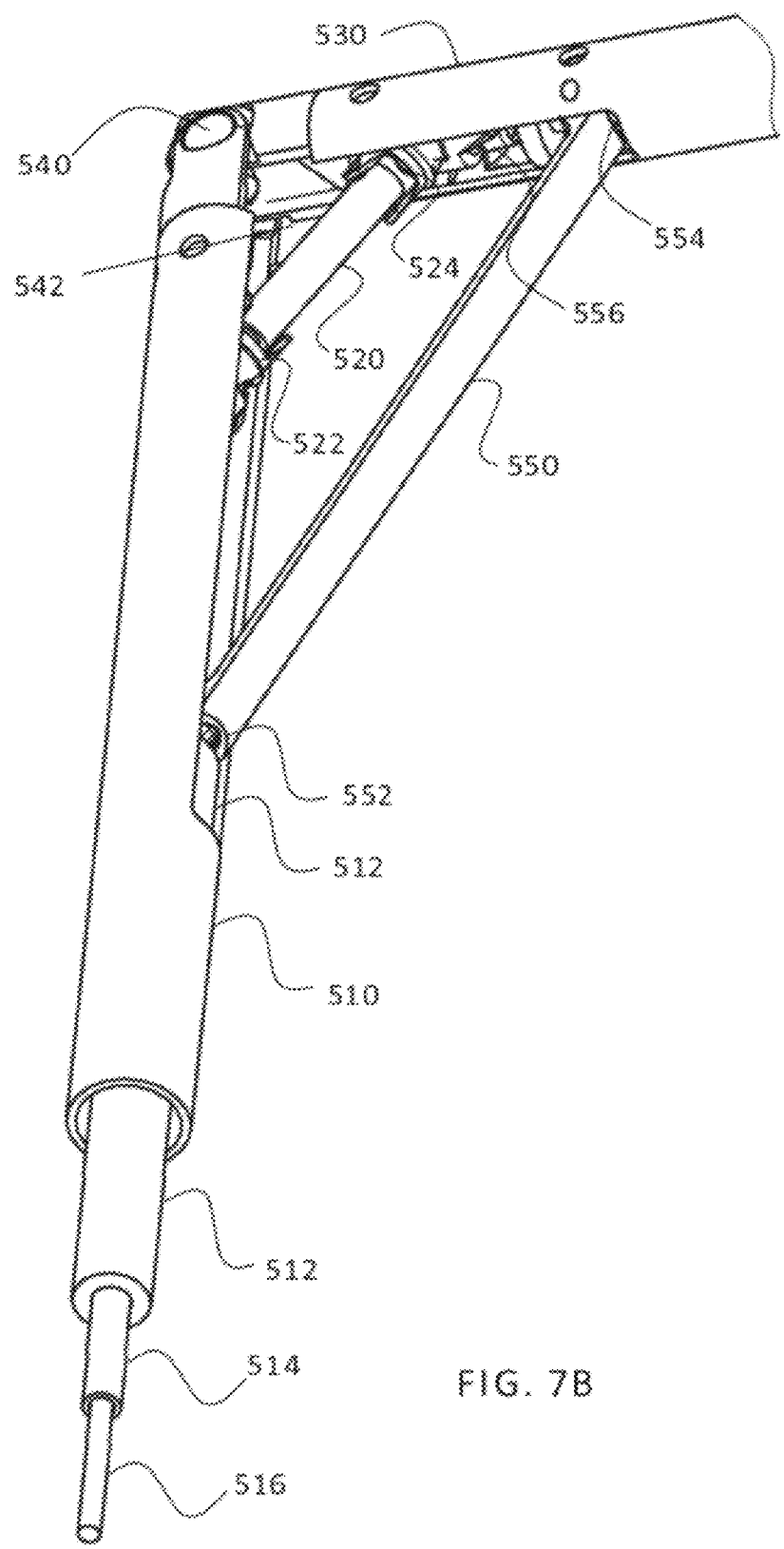
Figure 7C:
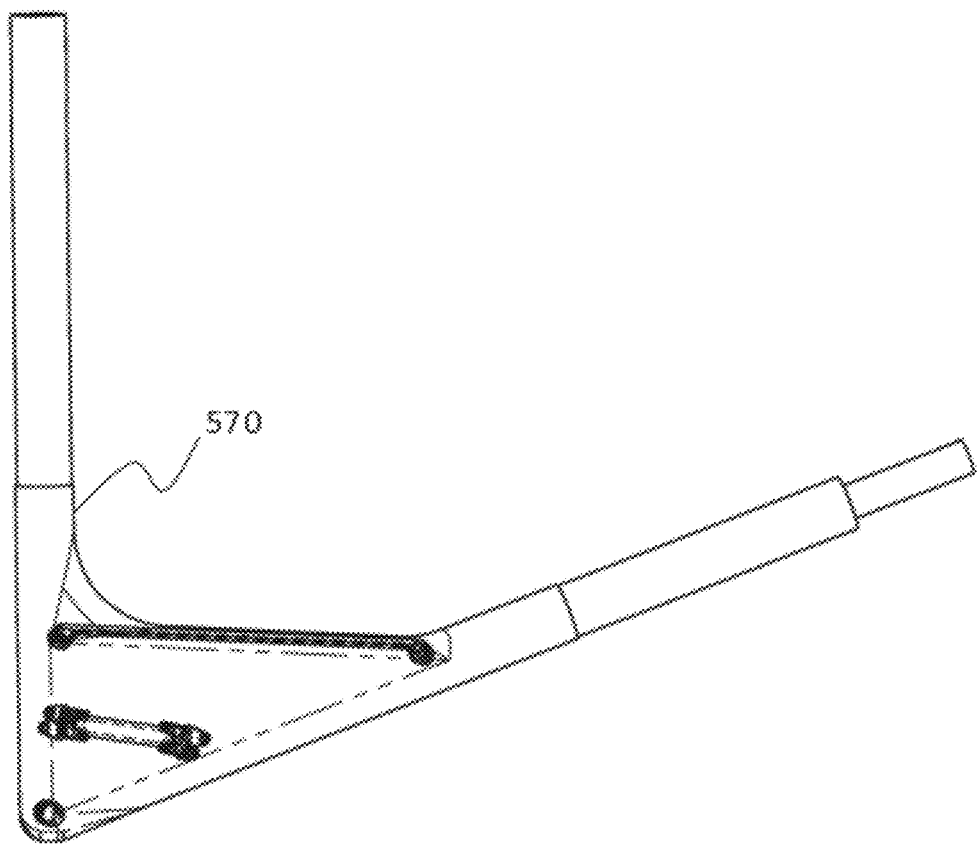

FIGS. 7A-7C illustrate a surgical instrument similar to the instrument described in FIG. 5 above, where flexible shaft 580 is replaced with a substantially rigid rod 520.

FIG. 7A illustrates a straight configuration where segments 510 and 530 form a substantially straight line and FIG. 5B shows an articulated configuration where segment 530 is bent towards segment 510.

Drive mechanism 520 is attached at a first end, optionally by a cardan joint 522, to a shaft 556 in proximal segment 510 and at a second end, optionally by a cardan joint 524, to a drive shaft (shown in FIG. 7B) in distal segment 530. In the straight configuration, drive mechanism 520 is located parallel to or within segments 510 and 530. Drive mechanism 520 extends from segments 510 and 530 in the articulated configurations.

In order to extend out of segments 510 and 530, drive mechanism 520 should be slidably attached to (or in) the proximal segment, so as to slide along the segment and compensate the distance at the point of attachment to the segment. In the embodiment shown in FIG. 7B, drive mechanism 520 is attached by cardan joint 522 to an inner tube 514 in segment 510. The distance of the point of attachment of drive mechanism 520 to inner tube 514 should be compensated as the articulation angle changes. A detailed explanation of exemplary distance compensation mechanism in accordance with exemplary embodiments of the invention is provided with respect to FIG. 10 below.

In the embodiments shown in FIGS. 7A-C, drive mechanism 520 is a shaft which is attached by cardan joints to tubes in segments 510 and 530. The cardan joints allow the transfer of rotary movement from proximal segment 510 to distal segment 530. Shaft 520 may be hollow so as to enable additional drive mechanisms to be gated therethrough, for example linear movement mechanism such as at least one wire 516 shown in FIG. 7B.

In some embodiments of the invention, a sheath 570 is provided covering the drive and articulation mechanisms, for example as shown in FIG. 7C. Sheath 570 prevents body tissues from being caught in the drive and articulation mechanisms. Sheath 570 is optionally made of a biocompatible material with a sufficient flexibility so as not to be damaged by the stretching forces applied to it during articulation, for example silicon or rubber.

Sheath 570 (or a similar sheath adapted for the specific configuration) may be provided in all embodiments of the present invention, for example in the embodiments shown in FIGS. 1-6.

In the embodiments of FIGS. 5-7, the space between the articulation hinge and the point of connection of the lever to the distal segment is lost, meaning that no medical tool can be positioned therein, thereby requiring a longer distal segment as opposed to the embodiments shown in FIGS. 1-4. Thus, the choice between a drive mechanism positioned in the articulation angle and a drive mechanism positioned underneath the articulation angle may depend on the medical tool used and/or the treatment performed. For example, when a tacker is positioned within the distal segment, a substantial section of the distal segment is used, while positioning forceps at the end of the distal segment does not require use of the entire length of the distal segment.

Figure 8:
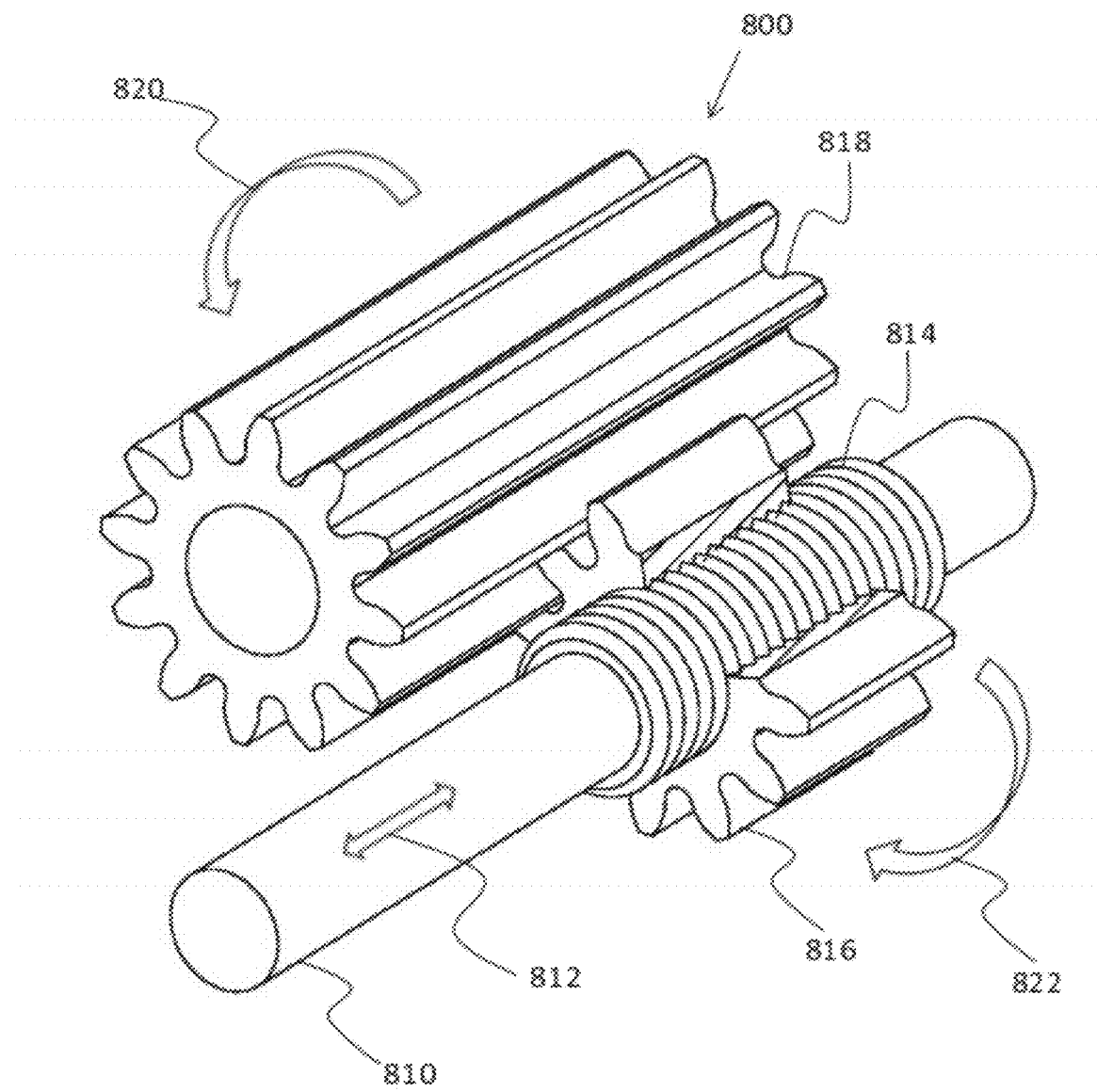
FIG. 8 is a schematic illustration of a linear distance compensation mechanism useful in a medical instrument in accordance with an exemplary embodiment of the invention.

An exemplary distance compensation mechanism 800 for a threaded element of a tacker is shown in FIG. 8. Distance compensation mechanism 800 consists of a tube or rod 810 whose linear position is to be controlled. Tube 810 represents for example a tube connected to threaded element 252 in FIG. 2A which is required to freely move in a linear direction (indicated as 812 in FIG. 8) during articulation of instrument 100 and should controllably move in a linear direction after articulation is completed in order to stab the needle in a body tissue.

Tube 810 comprises a screw-814 which is threaded inside a gear 816. Gear 816 engages a gear 818. Screw 814 and gear 816 are forced by spring to move along with tube 810 in the backward direction of 812 while gear 818 rotates but does not move linearly. After articulation is completed, and gear 816 is situated in its new position, the relative movement of tube 810 from it's current/new position is controlled by gear 818. When advancement of shaft 810 is required, gear 818 rotates in a direction 820 which rotates gear 816 in a direction 822 around screw-nut 814, thereby advancing tube 810. Opposite rotation is provided in order to return the needle backwards.

Figure 9A:
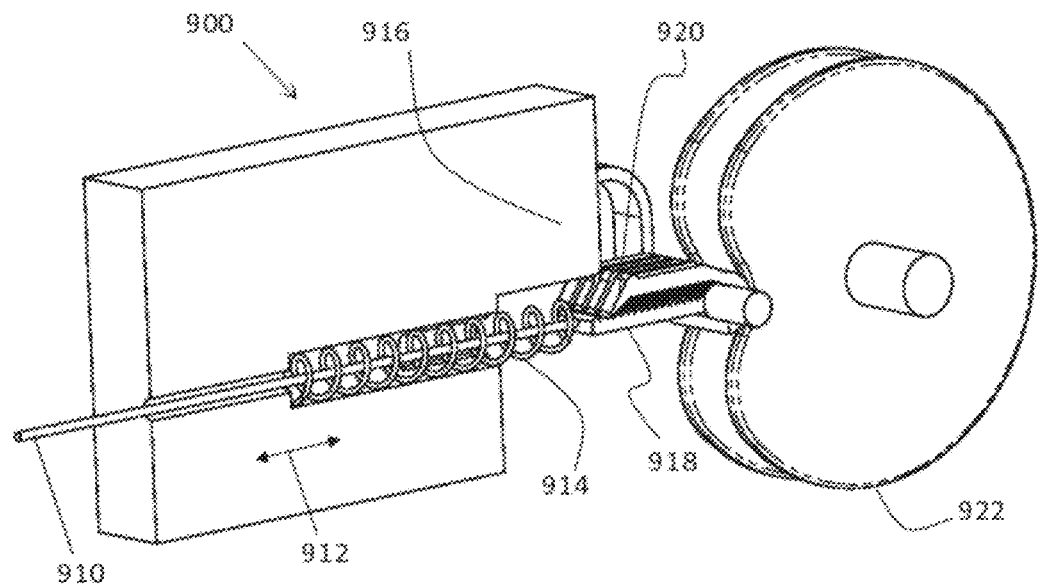
FIGS. 9A-9B are schematic illustrations of another linear distance compensation mechanism useful in a medical instrument in accordance with another embodiment of the invention.
Figure 9B:
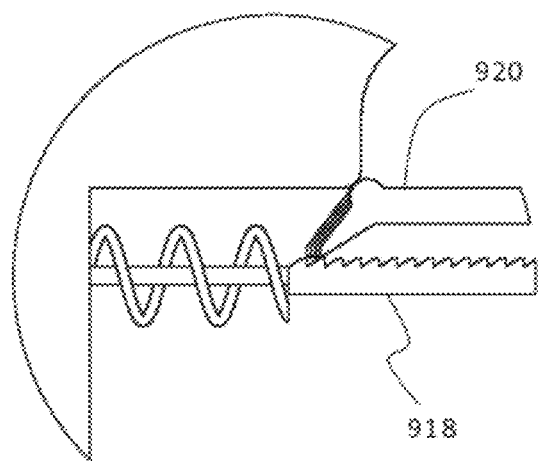

FIGS. 9A-B illustrate a distance compensation mechanism 900 for a threaded element of a tacker in accordance with another embodiment of the invention. Distance compensation mechanism 900 can be used as a replacement for mechanism 800 described above.

Mechanism 900 includes a tube 910 which slides along the direction 912 during articulation. Tube (or rod) 910 and a spring 914 surrounding the end of tube 910 are positioned in a receptacle 916. The end of tube 910 is attached to a saw-tooth plate 918. Finger like elements 920 are provided which after articulation is completed and tube 910 is within it's new position, engage with saw tooth plate 918 to provide controlled movement of tube 910 in the direction 912, for example to stab a needle in a body tissue. Teeth 920 are forced towards plate 918 by receptacle 916. A cam 922, or other mechanism, is provided for controllably advancing tooth plate 910 (and tube 910) after articulation is completed.

In some embodiments, the fingers of tooth plate 920 are slightly distant from each other in the direction 912 such that at any point of engagement of elements 920 with plate 918, at least one finger is provided in a tooth of plate, thereby blocking movement of plate 918 and applying force in a linear direction. FIG. 9 illustrates 4 teeth, however, any number of teeth may be used in accordance with embodiments of the invention. An increased number of teeth increases accuracy of the mechanism.

Figure 10:
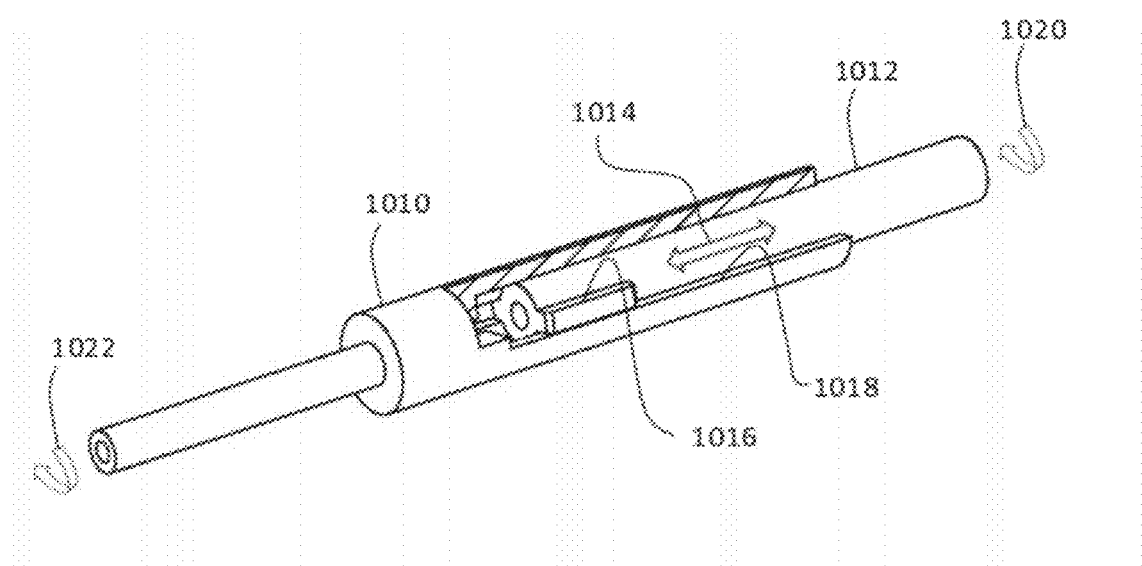
FIG. 10 is a schematic illustration of a distance compensation mechanism useful in a medical instrument in accordance with an embodiment of the invention.

FIG. 10 illustrates a distance compensation mechanism which enables variation of the length of a tube 1010 and enables rotation of a tube 1010 at varying longitudinal positions thereof. This may for example be required when compensating distance of tubes relating to the drive mechanism, such as tube 134 in FIGS. 1A-1E or tube 514 in FIG. 7B which are required to move linearly during articulation in order to vary the point of attachment of the drive mechanism and to remain steady after articulation is completed. A further requirement from tubes 134 and 514 is that they should be able to rotate at any longitudinal position thereof in order to transfer rotary motion from the proximal segment to the distal segment.

Tube 1010 includes a shaft 1012 within a portion of tube 1010 and extending therefrom. Shaft 1012 is moveable in the direction 1014, thereby varying the longitudinal position of tube 1010. Shaft 1012 optionally includes a male element 1016 engaged in a female element 1018 of tube 1010. The engagement of elements 1016 and 1018 enables a rotation of shaft 1012, for example in a direction 1020 to be transferred to rotation of tube 1010 in a direction 1022.

Reference is now made to handle 110 shown in FIG. 1. Handle 110 enables a user to control the articulation mechanism and one or more drive mechanisms of instrument 100. In some embodiments, handle 110 includes one or more mechanisms as illustrated in FIGS. 8 and 9.

Figure 11A:
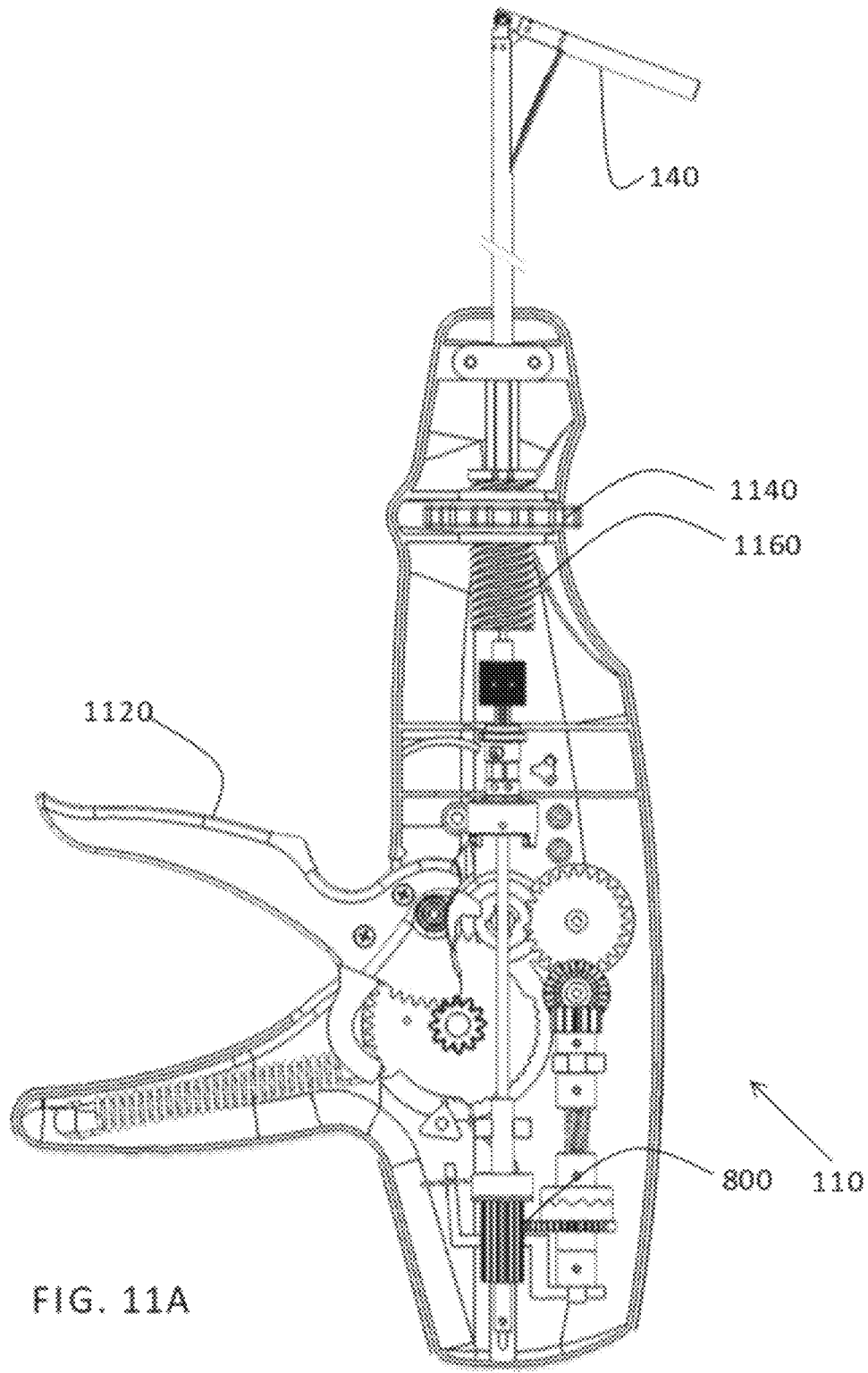
FIGS. 11A and 11B are partially sectioned view of a handle of a surgical instrument in accordance with exemplary embodiments of the invention.

FIG. 11A is a cross-sectional view of a handle 110 in accordance with an exemplary embodiment of the invention. Handle 110 comprises a grip 1120 for controlling the drive mechanism, for example. Distance compensation mechanism 800 is optionally provided for compensating distance of a threaded element of a tacker position in segment 140. Handle 110 may further comprise a screw nut 1140 around a screw 1160 for controlling articulation by pulling or pushing a lever. Other control mechanisms may be used in accordance with exemplary embodiments of the present invention. For example, in accordance with some embodiments, the drive mechanism and/or lever are motorized.

Figure 11B:
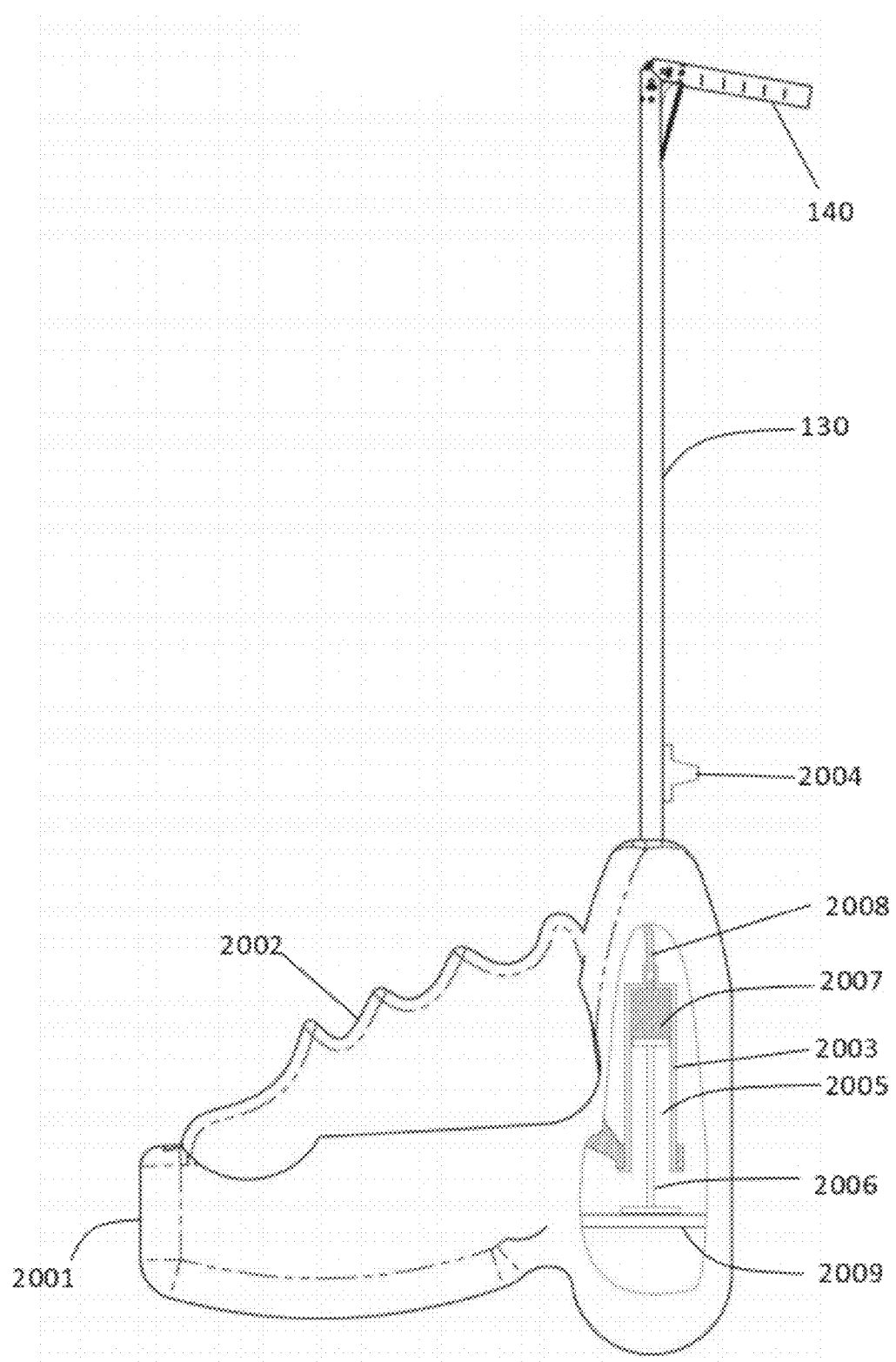

FIG. 11B is a partially cross sectional view of a handle 2001 used for actuation of a drive mechanism including a conduit in order to inject medication or collect tissue samples, for example as shown and described with respect to FIG. 5E. A handle 2004 positioned at the end of proximal segment 130 for linear movement of a syringe at the end of distal segment 130, as shown in FIG. 5E. An additional handle 2002 activates an injection device 2003 in handle 2001. Container 2005 includes medication 2007 and is attached at one end to a conduit 2008 and at the other end to a support 2009, attached to a rod 2006. In some embodiments, injection device 2003 functions as an aspiration device for collection of tissue samples. In these embodiments, an additional handle is provided which pushes rod 2006 to the proximal direction to create a vacuum within conduit 2008.

In some embodiments of the invention, an adaptor 120 is provided between handle 110 and proximal segment 130. Adaptor 120 may be used in order to use the instrument as an add-on to existing instruments, whereby an existing handle is connected to an adaptor and proximal and distal segments, and an existing medical tool is position within or at the distal segment.

Figure 12A:
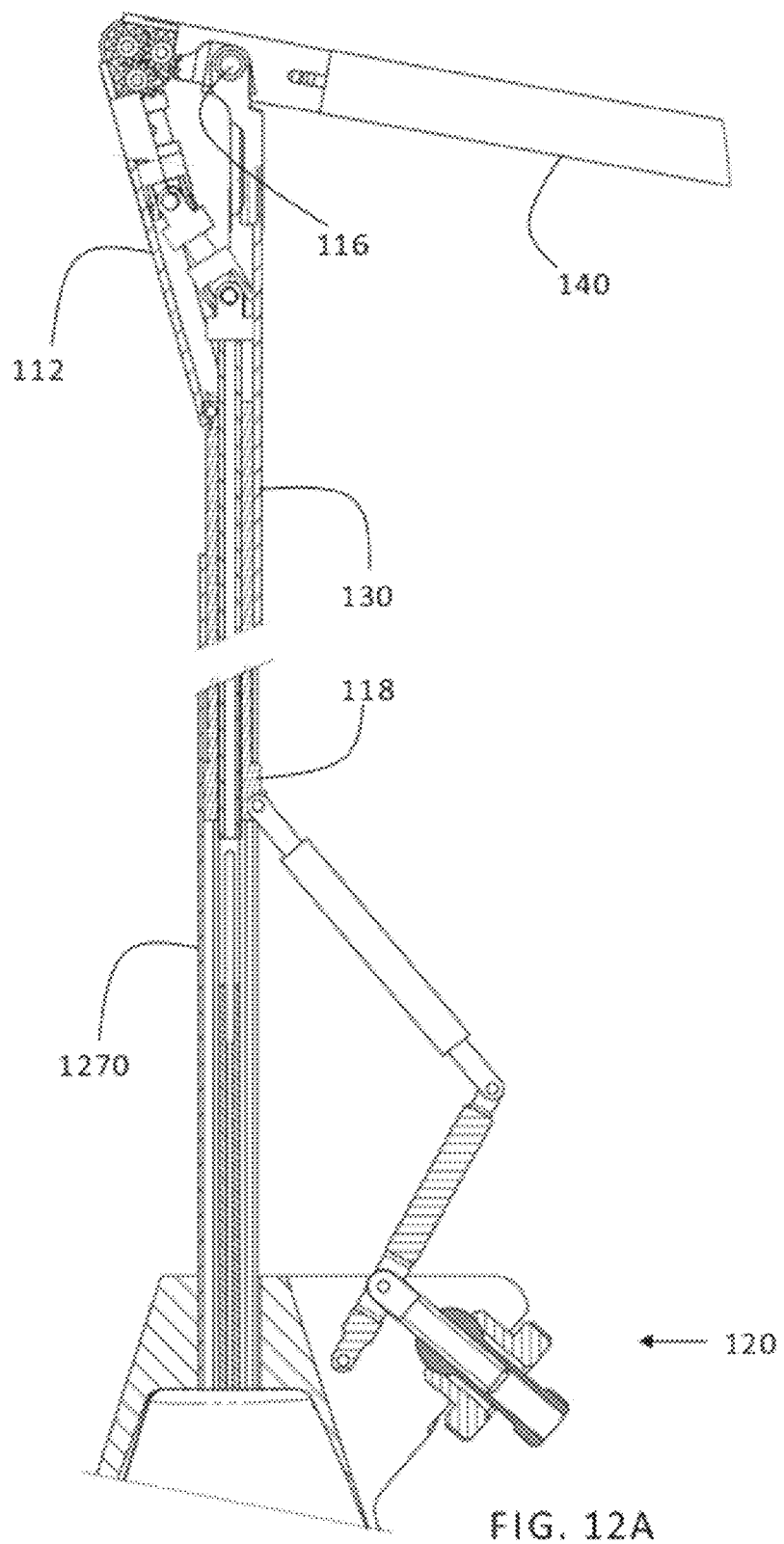
FIGS. 12A and 12B are partially sectioned views of an adaptor for a surgical instrument in accordance with an exemplary embodiment of the invention.
Figure 12B:
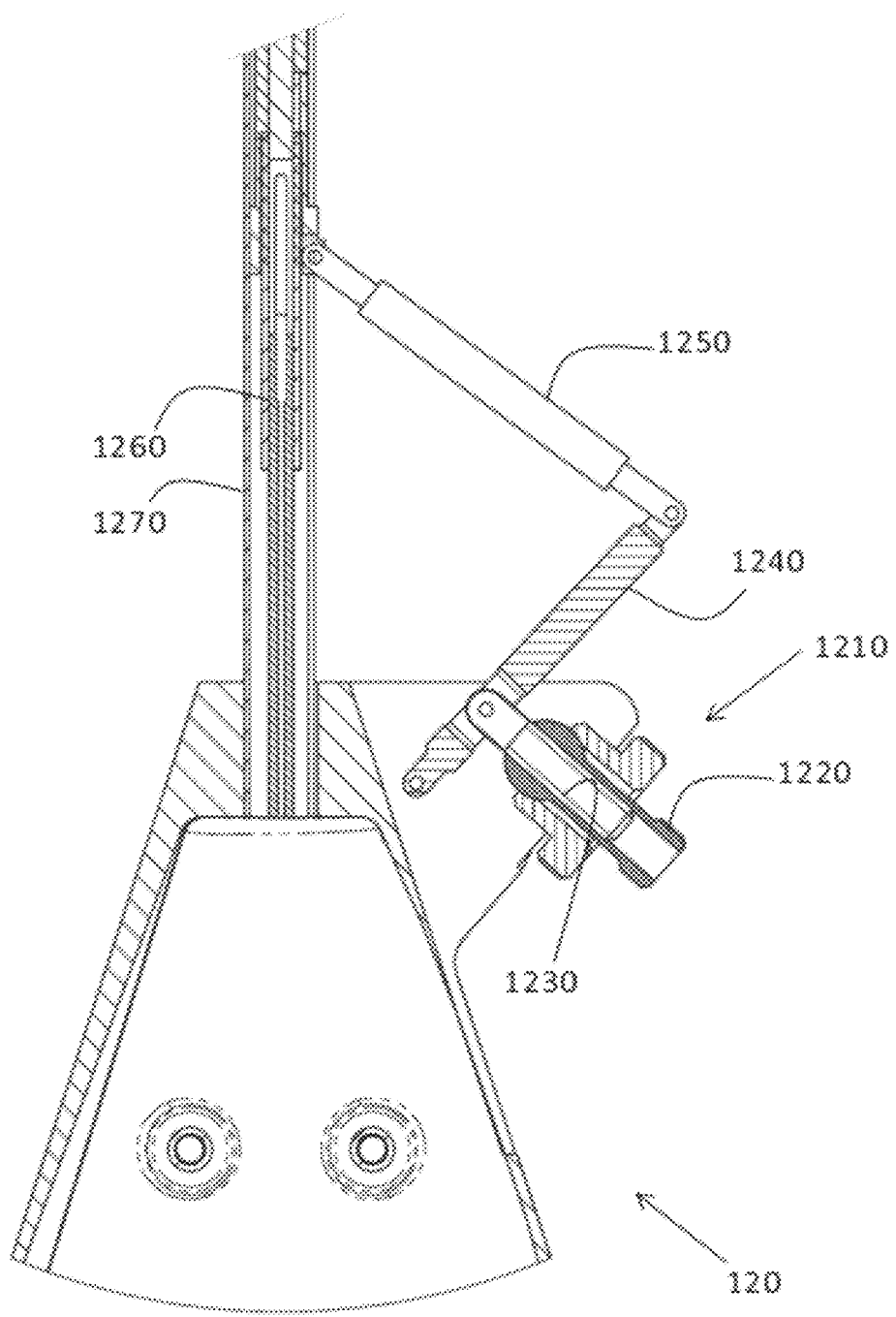
Figure 12C:
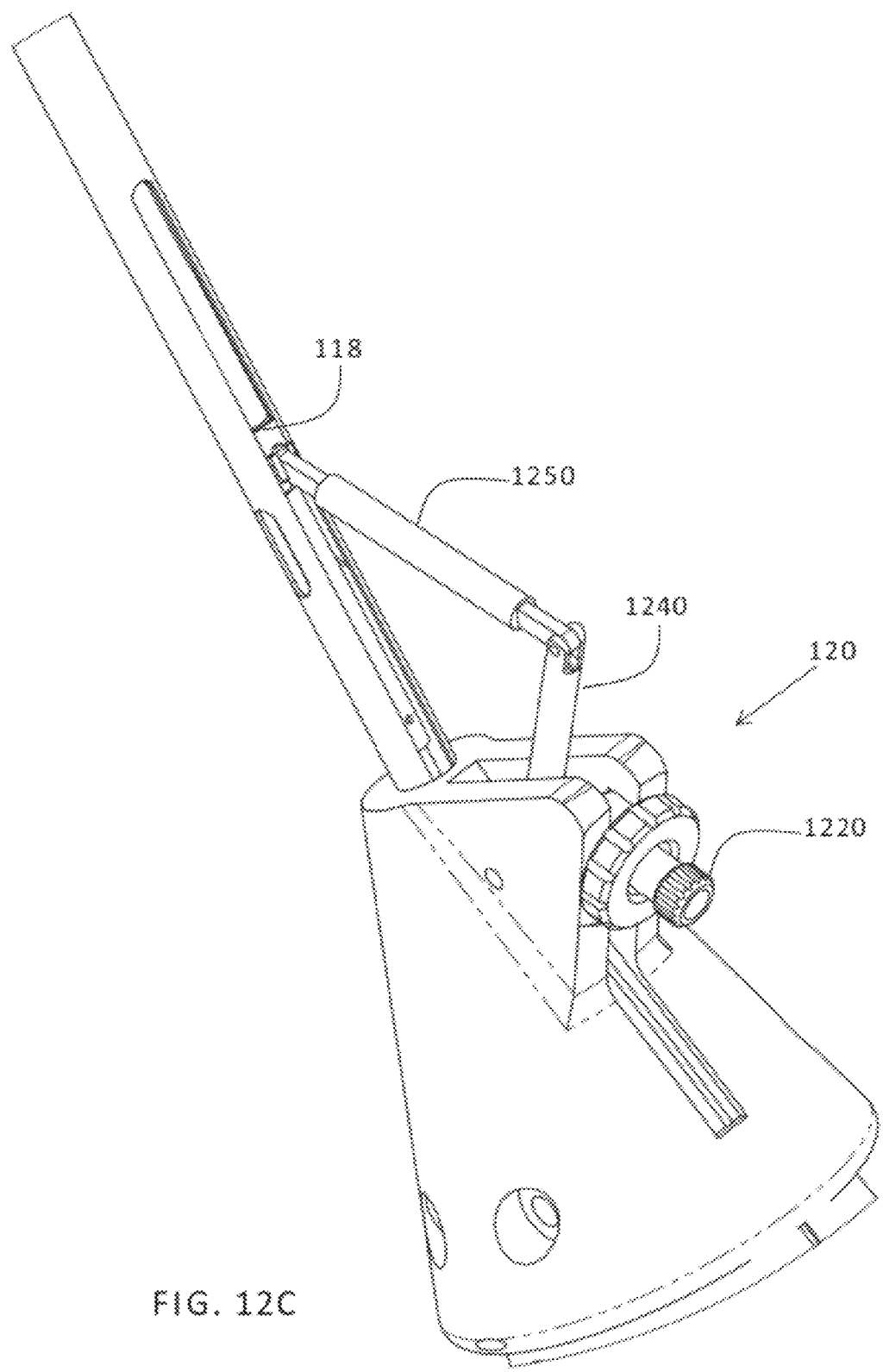
FIG. 12C is an upper view of the adaptor of FIGS. 12A and 12B.

FIGS. 12A-12C illustrate an adaptor in accordance with an exemplary embodiment of the invention. FIG. 12A is a partially cross sectional view of an instrument as shown and described with respect to FIG. 1. FIG. 12B is a closer view of the cross-section of the adaptor in FIG. 12A and FIG. 12C is an upper view of the adaptor.

Adaptor 120 includes a shaft 1270 which is attached to proximal segment 130. An articulation control mechanism 1210 is provided, consisting of a screw nut 1220 on a screw 1230 connected to a lever mechanism having a first lever 1240 and a second lever 1250 which are connected drive element 118. Rotation of screw-nut 1220 pushes (or pulls) first lever 1240 which pushes (or pulls) second lever 1250 which in turn pushes (or pulls) drive element 118 which pushes lever 112 and causes articulation of distal segment 140 around joint 116.

In some embodiments, control of the drive mechanism is transferred from the handle through the adaptor.

Although adaptor is described with respect to the embodiment of FIG. 1, it is understood that adaptor 120 may be used with any of the embodiments of the invention, for example, adaptor 120 may be used with the embodiment illustrated in FIG. 5 where second lever 1250 will be attached to drive element 536.

Throughout this application, specific embodiments of instrument are described for clarity with specific combination of articulation mechanisms, drive mechanism and medical tools. It is understood that embodiments of the present invention include any combination of the articulation mechanisms, drive mechanisms and medical tools described with respect to specific embodiments.

It is expected that during the life of a patent maturing from this application many relevant articulation and drive mechanisms will be developed and the scope of the terms articulation mechanism and/or drive mechanisms intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a joint" or "at least one joint" may include a plurality of joint, including interconnected links.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. For example, specific medical tools are described as used with specific embodiments of the invention, it is appreciated that any medical tool may be used with any of the exemplary embodiments described.

What is claimed is:

1. An articulating medical instrument comprising of:
   a proximal segment having a first distal end and a first proximal end;
   a distal segment having a second distal end and a second proximal end, the second proximal end connected to the first distal end of the proximal segment;
   an articulation mechanism for changing an articulation angle between the proximal and distal segments and providing a straight configuration in which the proximal and distal segments form a line and at least one articulated configuration in which the proximal and distal segments form an articulation angle of less than 180 degrees between the segments, the articulation mechanism being configured for increasing or decreasing the articulation angle; and
   one or more drive mechanisms configured for transferring rotation from the proximal segment to the distal segment, at least one drive mechanism being contained within the segments in the straight configuration, wherein in the articulated configuration at least a portion of the at least one drive mechanism performs at least one of (i) exits the distal segment between the distal and proximal ends thereof and (ii) exits the proximal segment between the distal and proximal ends thereof,
   wherein the articulation mechanism comprises a lever and wherein at least one of the drive mechanisms is positioned between the articulation angle and the lever,
   wherein the articulation mechanism and drive mechanisms are two separate mechanisms and wherein activation of the one or more drive mechanisms does not change the articulation angle.

2. An instrument according to claim 1, wherein at least one drive mechanism does not pass through the apex of the articulation angle.

3. An instrument according to claim 1, wherein at least one drive mechanism is positioned interior of the articulation angle.

4. An instrument according to claim 1, wherein the lever is positioned interior of the articulation angle.

5. An instrument according to claim 1, wherein at least one drive mechanism is configured to transfer linear movement from a proximal end of the instrument to a distal end of the instrument.

6. An instrument according to claim 1, wherein a medical tool is positioned in or at the distal segment and wherein the drive mechanism is configured to actuate the medical tool.

7. An instrument according to claim 1, further comprising a sheath covering the articulation mechanism and the drive mechanism.

8. An instrument according to claim 1, wherein the at least one drive mechanism for transferring rotation from the proximal segment to the distal segment comprises a gear mechanism.

9. An instrument according to claim 1, wherein the at least one drive mechanism for transferring rotation from the proximal segment to the distal segment comprises a flexible shaft.

10. An instrument according to claim 1, wherein the at least one drive mechanism for transferring rotation from the proximal segment to the distal segment comprises a spring.

11. An instrument according to claim 10, wherein a wire passes through said spring.

12. An instrument according to claim 1, wherein the proximal and distal segments are connected by a flexible joint.

13. An instrument according to claim 1, wherein the drive mechanism and articulation mechanism are not fixedly connected at the connection between the proximal and distal segments.

14. An instrument according to claim 1, wherein the drive mechanism is not affected by external forces applied against maintaining the articulation angle.

15. An instrument according to claim 1, further comprising a distance compensation mechanism for compensating the distance at the point of attachment of the drive mechanism to the distal and proximal segments in the articulated configuration as the articulation angle changes.

16. An articulating medical instrument according to claim 1, wherein the distal segment contains a threaded shaft around which a plurality of helical fasteners are screwed; and wherein the drive mechanism is configured for transferring rotary movement from the proximal segment to the distal segment such that the fasteners distally exit the threaded shaft.

17. An instrument according to claim 16, wherein the drive mechanism is positioned interior of the articulation angle.

18. An instrument according to claim 17, wherein the lever extends out of the proximal segment and wherein the drive mechanism is positioned between the articulation angle and the proximal segment.

19. An instrument according to claim 16, wherein the drive mechanism configured for transferring rotary movement from the proximal segment to the distal segment comprises a gear mechanism.

20. An instrument according to claim 16, wherein the drive mechanism configured for transferring rotary movement from the proximal segment to the distal segment comprises a flexible shaft.

21. An instrument according to claim 16, wherein the drive mechanism configured for transferring rotary movement from the proximal segment to the distal segment comprises a spring.

22. An instrument according to claim 21, wherein a wire passes through said spring.

23. An instrument according to claim 16, further comprising a distance compensation mechanism for compensating the distance at the point of attachment of the drive mechanism to the distal and proximal segments in the articulated configuration as the articulation angle changes.

24. An instrument according to claim 1, wherein the at least one drive mechanism is positioned exterior of the articulation angle.

25. An instrument according to claim 1, wherein the proximal and distal segments are straight segments.

26. An instrument according to claim 1 wherein the proximal and distal segments form an acute angle.

27. An instrument according to claim 1 wherein in the articulated configuration at least a portion of the at least one drive mechanism (i) exits the distal segment between the distal and proximal ends thereof and (ii) exits the proximal segment between the distal and proximal ends thereof.

28. An instrument according to claim 1, further comprising a sheath covering the drive mechanism at least at the portion outside the distal and proximal sections and wherein the drive mechanism comprises a flexible shaft rotating within the sheath.

29. An articulating medical instrument comprising of:
a proximal segment having a first distal end and a first proximal end;
a distal segment having a second distal end and a second proximal end, the second proximal end connected to the first distal end of the proximal segment;
an articulation mechanism for changing an articulation angle between the proximal and distal segments and providing a straight configuration in which the proximal and distal segments form a line and at least one articulated configuration in which the proximal and distal segments form an articulation angle of less than 180 degrees between the segments, the articulation mechanism being configured for increasing or decreasing the articulation angle; and
one or more drive mechanisms configured for transferring rotation from the proximal segment to the distal segment, at least one drive mechanism being contained within the segments in the straight configuration, wherein in the articulated configuration at least a portion of the at least one drive mechanism performs at least one of (i) exits the distal segment between the distal and proximal ends thereof and (ii) exits the proximal segment between the distal and proximal ends thereof,
wherein the articulation mechanism and drive mechanisms are two separate mechanisms and wherein activation of the one Of more drive mechanisms does not change the articulation angle.

* * * * *